United States Patent [19]
Ueno et al.

[11] Patent Number: 6,005,085
[45] Date of Patent: Dec. 21, 1999

[54] CONDENSED AZO COMPOUNDS AND PROCESS FOR PREPARING THE SAME

[75] Inventors: Ryuzo Ueno, Nishinomiya; Masaya Kitayama, Takarazuka; Kenji Minami, Sennan; Hiroyuki Wakamori, Hyogo-ken; Katsunori Tanikawa, Nishinomiya, all of Japan

[73] Assignee: Kabushiki Kaisha Ueno Seiyaku Oyo Kenkyujo, Osaka, Japan

[21] Appl. No.: 09/194,500

[22] PCT Filed: Mar. 19, 1998

[86] PCT No.: PCT/JP98/01166

§ 371 Date: Nov. 18, 1998

§ 102(e) Date: Nov. 18, 1998

[87] PCT Pub. No.: WO98/41580

PCT Pub. Date: Sep. 24, 1998

[30] Foreign Application Priority Data

Mar. 19, 1997 [JP] Japan .................................. 9-065995

[51] Int. Cl.$^6$ .................... C09B 33/147; C09B 67/20; C09D 11/00; C09D 7/12; C08J 3/20; G03G 5/06
[52] U.S. Cl. .................... 534/651; 534/657; 534/689; 534/797; 534/812; 534/820; 106/31.46; 106/31.52; 106/31.81; 106/31.78; 106/496; 524/89; 524/91; 524/95; 524/105; 524/111; 524/190; 548/261; 548/268.4; 548/305; 548/305.4; 548/444; 549/480; 560/45; 564/153

[58] Field of Search .................... 534/651, 657, 534/689, 797, 812, 820; 560/45; 564/153; 106/31.46, 31.81, 31.52, 31.78, 496; 524/190

[56] References Cited

U.S. PATENT DOCUMENTS

| | | | |
|---|---|---|---|
| 3,658,785 | 4/1972 | Ronco et al. | 534/820 |
| 4,051,121 | 9/1977 | Tcherkinsky et al. | 534/820 |
| 4,053,464 | 10/1977 | Roueche | 534/820 |
| 4,247,614 | 1/1981 | Ohta et al. | 534/820 X |

FOREIGN PATENT DOCUMENTS

| | | |
|---|---|---|
| 141645 | 9/1990 | China . |
| 7-238231 | 7/1995 | Japan . |
| 98/16458 | 4/1998 | WIPO . |
| 98/16587 | 4/1998 | WIPO . |

*Primary Examiner*—Fiona T. Powers
*Attorney, Agent, or Firm*—Sughrue, Mion, Zinn, Macpeak & Seas, PLLC

[57] ABSTRACT

The present invention provides novel condensed azo compounds using bisamide compounds of 2-hydroxynaphthalene-3,6-dicarboxylic acid, amide, or ester as the couplers, which have excellent properties such as excellent water resistance, chemical resistance, solvent resistance, and heat resistance.

12 Claims, 9 Drawing Sheets

CONDENSED AZO COMPOUNDS AND PROCESS FOR PREPARING THE SAME

TECHNICAL FIELD

The present invention relates to novel condensed azo compounds and a process for preparing the same.

BACKGROUND OF THE INVENTION

In recent years, novel pigments, dyes and the like have been actively developed in order to improve, for example, paints, inks, photosensitive materials by providing them with high added values or superior properties, in particular superior light resistance, solvent resistance, water resistance, and/or chemical resistance. As exempla of such compounds, condensed azo compounds prepared from bisamides of 2-hydroxynaphthalene-3-carboxylic acid (e.g., Chromophthal Scarlet RN or BRN, The Japanese Patent Publication No. S48-11205 B (1973)), and condensed azo compounds prepared from bisamides of 2-hydroxynaphthalene-6-carboxylic acid (e.g., The Japanese Patent Publication No. H7-238231 A (1995)) are already known.

DISCLOSURE OF THE INVENTION

The present invention is characterized in that it provides azo coloring materials having excellent properties such as excellent water resistance, chemical resistance, solvent resistance, and heat resistance. Furthermore, the present invention aims to provide a series of azo compounds of which color and vividness can be regulated by appropriately selecting the substituents on the molecules.

The present invention provides novel condensed azo compounds using bisamide compounds prepared from 2-hydroxynaphthalene-3,6-dicarboxylic acid as couplers, as well as coloring materials comprising the same, and a process for preparing said condensed azo compounds. In particular, the present invention relates to a condensed azo compound represented by the general formula [I], [II], or [III]:

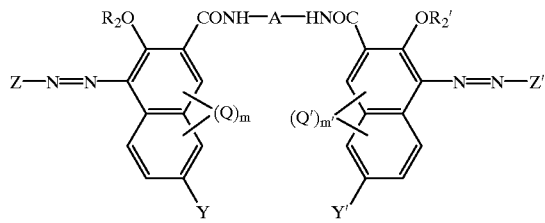

[I]

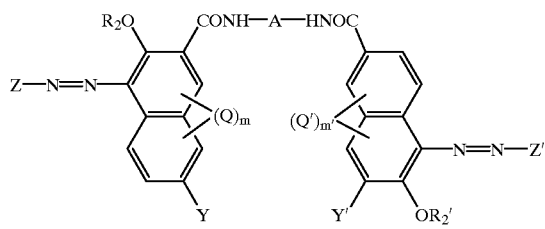

[II]

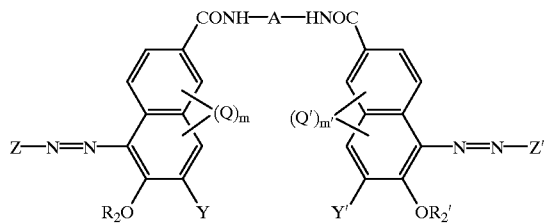

[III]

wherein, Y represents —$(CONH)_n$—X or —COR;

Y' represents —$(CONH)_n$—X' or —COR';

X and X' each represent an optionally branched alkyl group of 1–16 carbon atoms, an optionally substituted aromatic group, or an optionally substituted heterocyclic group having conjugated double bonds;

n represents an integer 1 or 2;

R and R' each represent a hydroxyl group, an optionally branched alkoxy group of 1–30 carbon atoms, a benzyloxy group, a phenyloxy group, or a phenacyloxy group, provided that if one of R and R' is a hydroxyl group, then it may form an acceptable salt;

$R_2$ and $R_2'$ each represent a hydrogen atom, an optionally branched alkyl group of 1–6 carbon atoms, an acyl group of 1–6 carbon atoms, or a phenylalkyl group;

Q and Q' each represent an optionally branched alkyl group of 1–6 carbon atoms, an optionally branched alkoxy group of 1–6 carbon atoms, a halogen atom, a nitro group, or a nitroso group;

m and m' each represent an integer from 0 to 3, provided that if m or m' is 1, then Q or Q' may bind to either of the two fused rings, and if m or m' is 2 or 3, then Q or Q' may bind to one or both of the fused rings or may form a ring together with the two fused rings;

A represents an optionally branched alkylene group of 2–12 carbon atoms or a cyclic group having conjugated double bonds; and Z and Z' each represent an optionally substituted monovalent aromatic group, as well as to a process for preparing the same, and coloring materials comprising such condensed azo compound. The azo compound of the present invention has non-condensed amide group(s), hydroxyl group(s), or alkoxy group(s), and in particular when the amide group is an aromatic amide group, color and vividness of the compound can be regulated by introducing an appropriate substituent(s) into such aromatic group. As used herein, the term "coloring materials" refers to, for example, dyes, pigments, inks, paints, printing inks, and organic photoconductive materials.

Furthermore, the present invention relates to a process for preparing a condensed azo compound represented by the general formula [I], [II], or [III]:

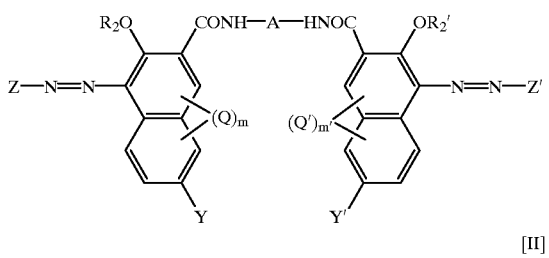

[I]

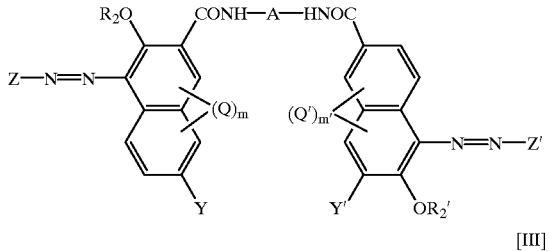

[II]

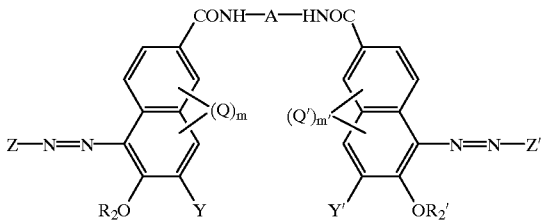

[III]

wherein, Y represents —(CONH)$_n$—X or —COR;

Y' represents —(CONH)$_n$—X' or —COR';

X and X' each represent an optionally branched alkyl group of 1–16 carbon atoms, an optionally substituted aromatic group, or an optionally substituted heterocyclic group having conjugated double bonds;

n represents an integer 1 or 2;

R and R' each represent a hydroxyl group, an optionally branched alkoxy group of 1–30 carbon atoms, a benzyloxy group, a phenyloxy group, or a phenacyloxy group, provided that if one of R and R' is a hydroxyl group, then it may form an acceptable salt;

R$_2$ and R$_2$' each represent a hydrogen atom, an optionally branched alkyl group of 1–6 carbon atoms, an acyl group of 1–6 carbon atoms, or a phenylalkyl group;

Q and Q' each represent an optionally branched alkyl group of 1–6 carbon atoms, an optionally branched alkoxy group of 1–6 carbon atoms, a halogen atom, a nitro group, or a nitroso group;

m and m' each represent an integer from 0 to 3, provided that if m or m' is 1, then Q or Q' may bind to either of the two fused rings, and if m or m' is 2 or 3, then Q or Q' may bind to one or both of the fused rings or may form a ring together with the two fused rings;

A represents an optionally branched alkylene group of 2–12 carbon atoms or a cyclic group having conjugated double bonds; and Z and Z' each represent an optionally substituted monovalent aromatic group; the process being characterized in that an aromatic diazonium compound represented by the general formula [VII] or [VII']:

 [VII]

 [VII']

wherein Z and Z' each represent an optionally substituted monovalent aromatic group,
is coupled with a bisamide compound represented by the general formula [VIII], [IX], or [X]:

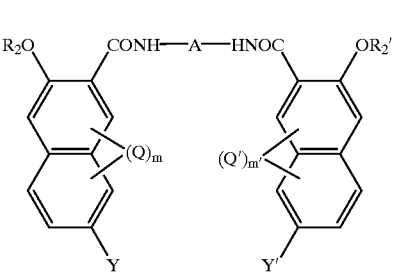

[VIII]

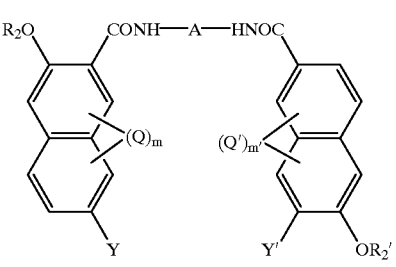

[IX]

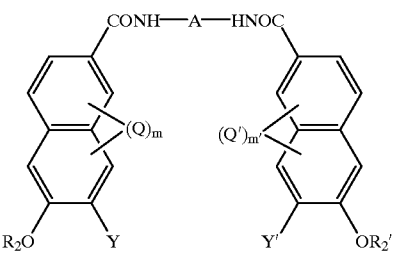

[X]

wherein, Y represents —(CONH)$_n$—X or —COR;

Y' represents —(CONH)$_n$—X' or —COR';

X and X' each represent an optionally branched alkyl group of 1–16 carbon atoms, an optionally substituted aromatic group, or an optionally substituted heterocyclic group having conjugated double bonds;

n represents an integer 1 or 2;

R and R' each represent a hydroxyl group, an optionally branched alkoxy group of 1–30 carbon atoms, a benzyloxy group, a phenyloxy group, or a phenacyloxy group, provided that if one of R and R' is a hydroxyl group, then it may form an acceptable salt;

R$_2$ and R$_2$' each represent a hydrogen atom, an optionally branched alkyl group of 1–6 carbon atoms, an acyl group of 1–6 carbon atoms, or a phenylalkyl group;

Q and Q' each represent an optionally branched alkyl group of 1–6 carbon atoms, an optionally branched alkoxy group of 1–6 carbon atoms, a halogen atom, a nitro group, or a nitroso group;

m and m' each represent an integer from 0 to 3, provided that if m or m' is 1, then Q or Q' may bind to either of the two fused rings, and if m or m' is 2 or 3, then Q or Q' may bind to one or both of the fused rings or may form a ring together with the two fused rings; and A represents an optionally branched alkylene group of 2–12 carbon atoms or a cyclic group having conjugated double bonds.

The present invention also relates to novel bis (aminocarbonylnaphthol) derivatives represented by the general formula [VIII'], [IX'], or [X']:

A represents an optionally branched alkylene group of 2–12 carbon atoms or a cyclic group having conjugated double bonds;

provided that, at least one of Y and Y' comprises X or X' which is an optionally branched alkyl group of 1–16 carbon atoms.

The present invention further relates to novel bis (aminocarbonylnaphthol) derivatives represented by the general formula [VIII"], [IX"], or [X"]:

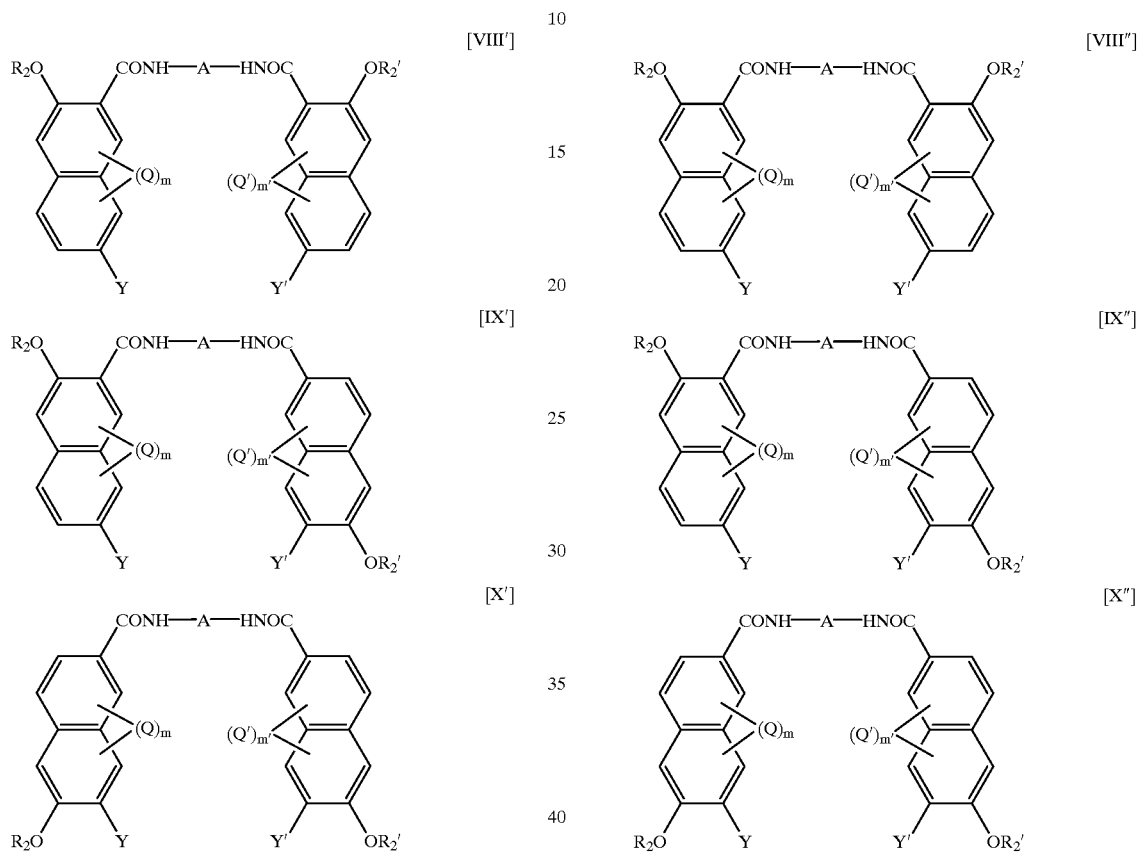

wherein, Y represents —(CONH)$_n$—X or —COR;
Y' represents —(CONH)$_n$—X' or —COR';
X and X' each represent an optionally branched alkyl group of 1–16 carbon atoms, an optionally substituted aromatic group, or an optionally substituted heterocyclic group having conjugated double bonds;
n represents an integer 1 or 2;
R and R' each represent a hydroxyl group, an optionally branched alkoxy group of 1–6 carbon atoms, a benzyloxy group, a phenyloxy group, or a phenacyloxy group, provided that if one of R and R' is a hydroxyl group, then it may form an acceptable salt;
$R_2$ and $R_2$' each represent a hydrogen atom, an optionally branched alkyl group of 1–6 carbon atoms, an acyl group of 1–6 carbon atoms, or a phenylalkyl group;
Q and Q' each represent an optionally branched alkyl group of 1–6 carbon atoms, an optionally branched alkoxy group of 1–6 carbon atoms, a halogen atom, a nitro group, or a nitroso group;
m and m' each represent an integer from 0 to 3, provided that if m or m' is 1, then Q or Q' may bind to either of the two fused rings, and if m or m' is 2 or 3, then Q or Q' may bind to one or both of the fused rings or may form a ring together with the two fused rings; and wherein, Y represents —(CONH)$_n$—X or —COR;
Y' represents —(CONH)$_n$—X' or —COR';
X and X' each represent an optionally branched alkyl group of 1–16 carbon atoms, an optionally substituted aromatic group, or an optionally substituted heterocyclic group having conjugated double bonds;
n represents an integer 1 or 2;
R and R' each represent a hydroxyl group, an optionally branched alkoxy group of 7–30 carbon atoms, a benzyloxy group, a phenyloxy group, or a phenacyloxy group, provided that if one of R and R' is a hydroxyl group, then it may form an acceptable salt;
$R_2$ and $R_2$' each represent a hydrogen atom, an optionally branched alkyl group of 1–6 carbon atoms, an acyl group of 1–6 carbon atoms, or a phenylalkyl group;
Q and Q' each represent an optionally branched alkyl group of 1–6 carbon atoms, an optionally branched alkoxy group of 1–6 carbon atoms, a halogen atom, a nitro group, or a nitroso group;
m and m' each represent an integer from 0 to 3, provided that if m or m' is 1, then Q or Q' may bind to either of the two fused rings, and if m or m' is 2 or 3, then Q or Q' may bind to one or both of the fused rings or may form a ring together with the two fused rings; and A represents an optionally branched alkylene group of 2–12 carbon atoms or a cyclic group having conjugated double bonds;

provided that, at least one of Y and Y' comprises R or R' which is an optionally branched alkoxy group of 7–30 carbon atoms.

The compound of the present invention is characterized in that it is a novel condensed azo compound of which fundamental structure comprises a bisamide compound (e.g., PCT/JP97/03638) derived from a naphthol having carboxyl groups at the 3- and 6-positions by amidating one of the carboxyl groups with an aromatic diamine.

In the present invention, A is an optionally branched alkylene group of 2–12 carbon atoms or a cyclic group having conjugated double bonds. The alkylene group is preferably straight, and those groups which consist of 2–6 carbon atoms are particularly preferred. Preferred cyclic groups having conjugated double bonds are arylene groups and those groups having fundamental structures represented by the general formula [IV]:

  [IV]

[wherein, Ar and Ar' each represent independently an optionally substituted arylene group or a heterocyclic group having conjugated double bonds;

M represents a single bond, or a group selected from —CH$_2$—, —CH=C(E)— (wherein E may represent, for example, hydrogen, a halogen atom, a lower alkyl group, or a cyano group), —O—, —S—, —S—S—, —CO—, —COO—, —SO$_2$—, —N(T)— (wherein T represents an optionally substituted phenyl group or a lower alkyl group), —N=N—, —CH=CH—φ—CH=CH— (wherein φ represents an arylene group), and the formula [V]:

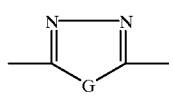  [V]

(wherein G represents —O—, —S—, or —NH—)], or the general formula [VI]:

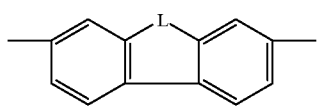  [VI]

[wherein L represents >N—CH$_3$, >C=O, or >C=S.]

Specific examples of such A are as follows:

(1) arylene groups, for example, phenylene, naphthylene, and anthrylene, which may be optionally substituted;

(2) —Ar—M—Ar'— groups, examples of which are where M is a single bond,

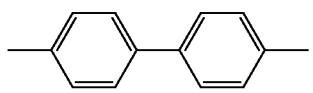

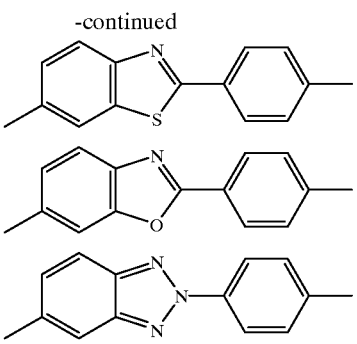

where M is —CH$_2$—,

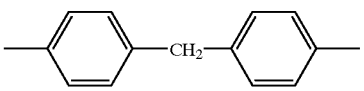

where M is —CH=C(E)—,

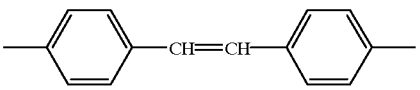

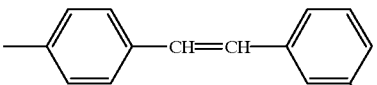

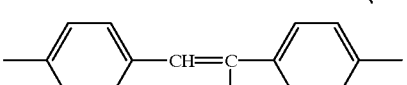

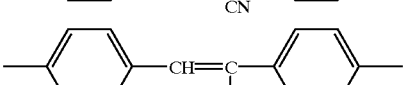

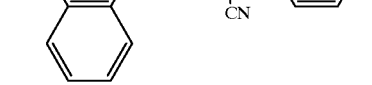

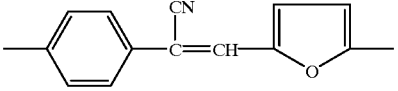

where M is —O—, —S—, —S—S—, —COO—, —SO$_2$—, —N(T)—, or —N=N—,

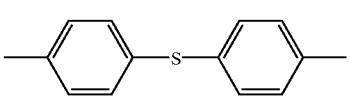

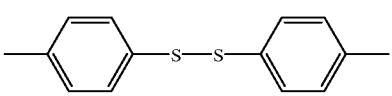

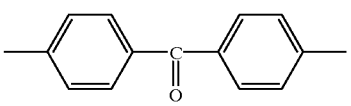

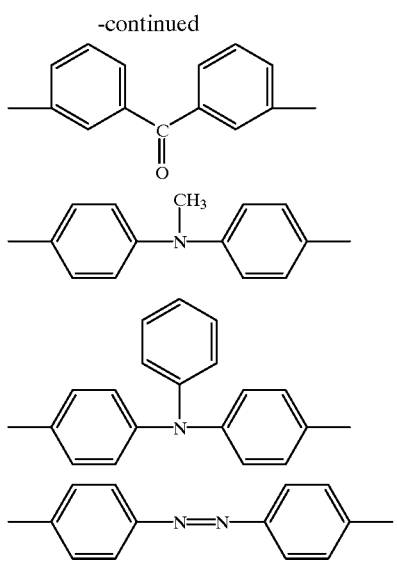

where M is —CH=CH—φ—CH=CH—,

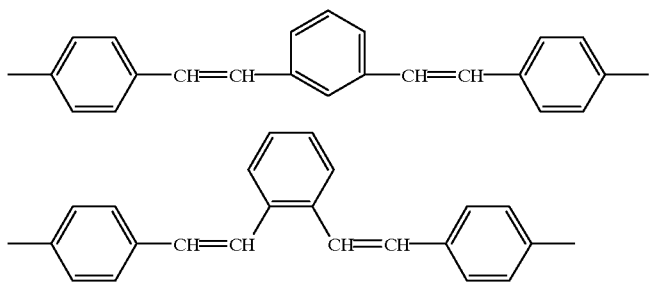

and where M is represented by the formula [V],

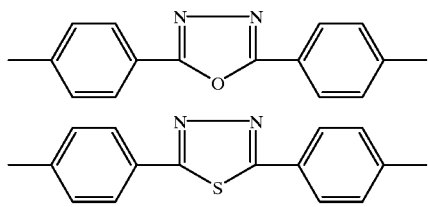

(3) an example of A having the fundamental structure represented by the general formula [VI] is

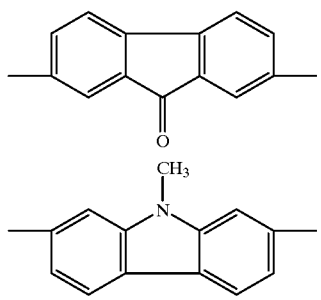

Examples of substituents on A may include lower alkyl groups such as methyl, ethyl, isopropyl, propyl, n-butyl, isobutyl, and tert-butyl, lower alkoxy groups such as methoxy and ethoxy, halogens such as fluorine, chlorine, bromine, and iodine, cyano, and nitro.

In Y and Y', the moiety constituting the group X or X' is, for example, an optionally branched alkyl group of 1–16, and preferably 1–12, carbon atoms, an optionally substituted aromatic group such as phenyl, naphthyl, or anthraquinonyl group, or an optionally substituted heterocyclic group having conjugated double bonds such as benzimidazolonyl, carbazolyl, pyridyl, thiazolyl, benzothiazolyl, imidazolyl, indolyl, thiofuryl phenothiazinyl, acridinyl, or quinolinyl group, provided that in the general formulas [VIII'], [IX'], and [X'], at least one of Y and Y' comprises X or X' which is an optionally branched alkyl group of 1–16 carbon atoms.

Examples of substitutes on such aromatic or heterocyclic groups may include halogens, nitro, lower alkyl, lower alkoxy, cyano, phenoxy, and amide (e.g., phenylaminocarbonyl) groups, and such phenoxy and amide groups may further have additional substituent(s) such as halogen, lower alkyl, lower alkoxy, alkylaminosulfonyl, and nitrile. Since color and vividness of the compounds can be effectively changed by introducing different kinds of substituent onto these aromatic or heterocyclic groups, a series of azo compounds having different color and/or vividness can be easily obtained.

Alternatively, Y and Y' may also represent COR or COR'. R and R' each represent a hydroxyl group, an optionally branched alkoxy group of 1–30, and preferably 1–20, carbon atoms (with the proviso that in the general formulas [VIII'], [IX'], and [X'], they each represent an optionally branched alkoxy group of 1–6, and preferably 1–4, carbon atoms, and in the general formulas [VIII"], [IX"], and [X"], they each represent an optionally branched alkoxy group of 7–30, and preferably 7–20, carbon atoms), a benzyloxy group, a phenoxy group, or a phenacyloxy group, and the aromatic rings contained in such groups may have substituent(s), provided that in the general formulas [VIII"], [IX"], and [X"], at least one of Y and Y' comprise R or R' which represents an optionally branched alkoxy group of 7–30 carbon atoms.

It is preferred that Y and Y' are —CONH—X and —CONH—X', respectively.

The groups $R_2$ and $R_2'$ is each a hydrogen atom, an optionally branched alkyl group of 1–6, and preferably 1–4, carbon atoms, with a methyl or ethyl group being preferred; an acyl group of 1–6, preferably 1–4, carbon atoms, and in particular an acetyl group; or a phenylalkyl group which may optionally have substituent(s) such as a halogen atom or a lower alkyl group of which number of carbon atoms is preferably 1–6.

Z and Z' constituting the azo groups are each an optionally substituted monovalent aromatic group. This aromatic group may be a fused ring with heterocyclic group(s). Typical examples of such group are phenyl, naphthyl, anthryl, indenyl, fluorenyl, indolyl, benzothiazolyl, quinolinyl, and carbazolyl groups. Examples of the substituent are halogens, lower alkyl, in particular methyl, cyano, nitro, alkoxy, amide, sulfo, alkylaminosulfonyl, aminocarbonyl, phenoxy, alkoxycarbonyl, hydroxy, and benzoylamino groups. A particularly preferred aromatic group is a phenyl group.

In the present invention, the two naphthalene nuclei each may be substituted with Q or Q' which may each represent, for example, any of a lower alkyl groups (preferably of 1–4 carbon atoms), a lower alkoxy group (preferably of 1–4 carbon atoms), a halogen atom, a nitro group and a nitroso group. Although the number of such substituents m or m' is usually 0, it may be up to 3. In this connection, the naphthol must not have such substituent at the 1-position.

The condensed azo compounds of the present invention may be prepared, for example, according to the reaction scheme described below. Although the following reaction scheme relates to condensed azo compounds [I'] in which the carboxyl groups at the 3-positions have been bisamidated by way of example, the condensed azo compounds of the formulas [II] and [III] may also be prepared in the similar manner.

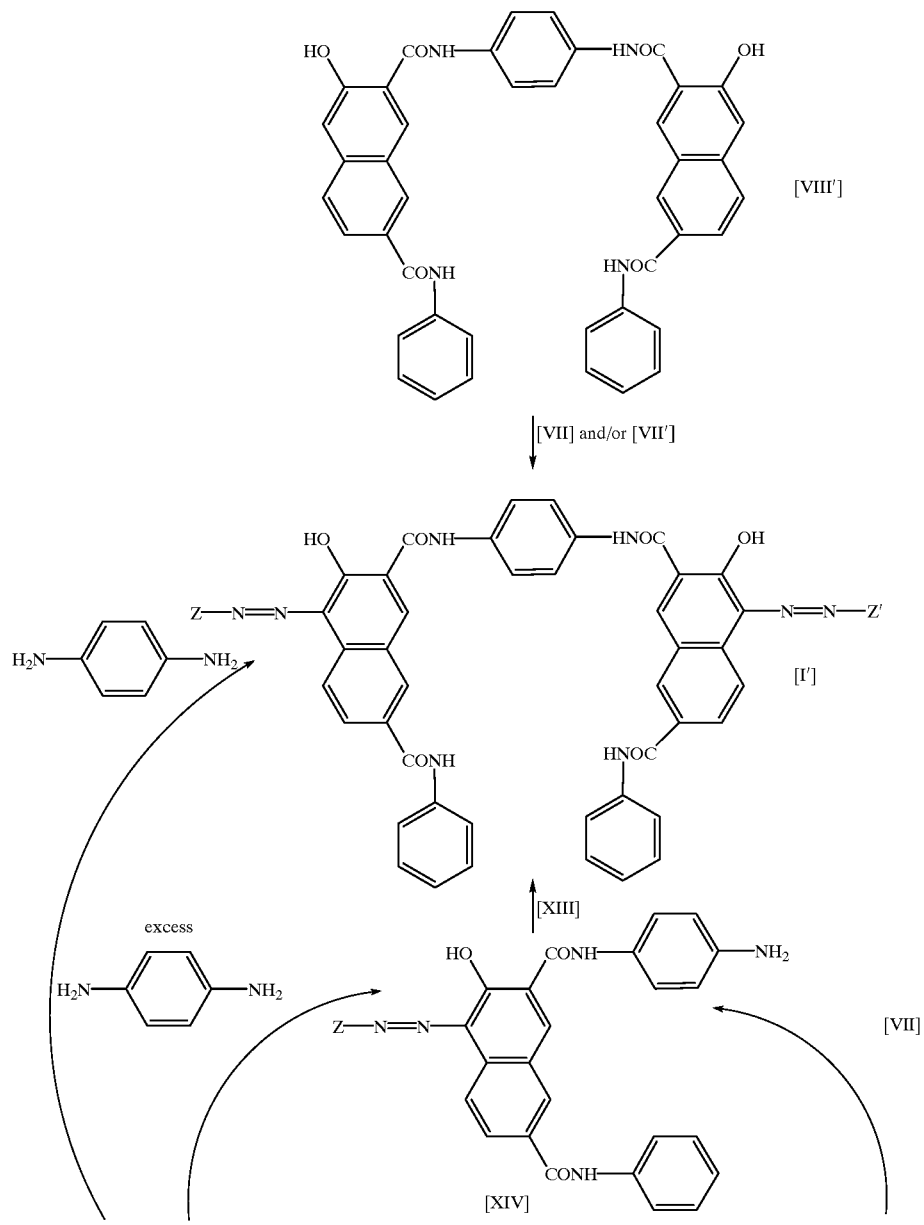

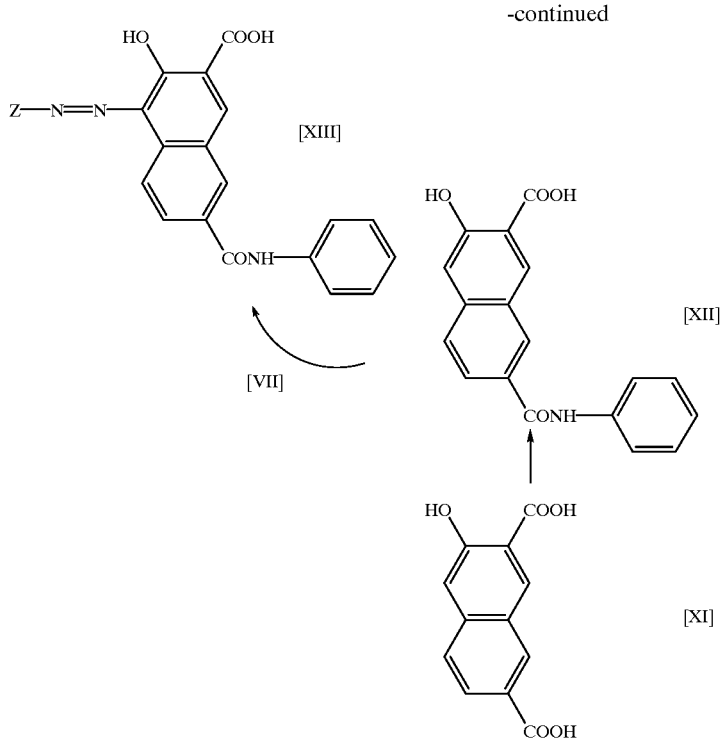
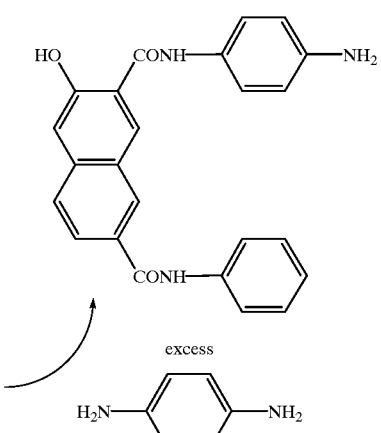

The bisamide compound [VIII'] is reacted with a diazonium compound to yield the condensed azo compound [I']. Alternatively, starting with 2-hydroxynaphthalene-3,6-dicarboxylic acid [XI] obtained by Kolbe-Schmitt or other reaction, the carboxyl group at the 3-position is protected by, for example, esterification. The carboxylic acid at the 6-position is converted into the acid chloride using thionyl chloride or the like, and then reacted with an aromatic amine to yield 6-amide compound [XII]. The dicarboxylic acid [XI] may also be directly reacted with amines using, for example, phosphorus trichloride or dicyclohexylcarbodiimide to obtain the amide compound. The amide compound thus obtained is reacted with a diazonium compound to yield 1-azo-6-amide compound [XIII] which is then, following if desired the conversion of the carboxyl group at the 3-position into the acid chloride, reacted with an aromatic diamine (e.g., phenylenediamine) to yield the condensed azo compound [I'].

Alternatively, the above reaction may be conducted with an excess of phenylenediamine to obtain the monoamine compound [XIV]. This monoamine compound [XIV] may also be obtained by subjecting the 6-amide compound [XII] to a condensation reaction with an excess of phenylenediamine before the reaction with a diazo compound, and then reacting with a diazonium compound.

Instead of phenylenediamine, a phenyl amine having a nitro group may be reacted with the 3-carboxyl group of the 6-amide compound [XII] in the presence of phosphorus trichloride and sulfolane to yield 3-(nitrophenylamide) compound, and the nitro group reduced into an amino group using a conventional method. This product may be then reacted with the 6-amide compound [XII] or corresponding acid chloride to yield a bisamide compound which may be then reacted with a diazonium compound to obtain the condensed azo compound [I'].

As described above, the reaction between a carboxyl group and an amino group of aromatic amine may be achieved by firstly converting the carboxyl group into the acid chloride followed by the reaction with the amine, or by directly reacting the carboxyl group with the aromatic amine in the presence of phosphorus trichloride and sulfolane. These reactions are just representative procedures to which the invention is not restricted.

Examples of the amine, that is, the compound constituting the group X or X', may include optionally substituted aromatic amino compounds such as aniline (X or X' is a phenyl group), α- or β-aminonaphthalene (X or X' is a naphthyl group), and aminoanthraquinone (X or X' is an anthraquinonyl group), optionally substituted heterocyclic compounds having conjugated double bonds such as aminobenzimidazolone (X or X' is a benzimidazolonyl group), aminocarbazole (X or X' is an aminocarbazolyl group), aminopyridine (X or X' is a pyridyl group), aminothiazole (X or X' is a thiazolyl group), aminobenzothiazole (X or X' is a benzothiazolyl group), and aminoimidazole (X or X' is an imidazolyl group), as well as aminoindole (X or X' is an indolyl group), aminothiophene (X or X' is a thiofuryl group), aminophenothiazine (X or X' is a phenothiazinyl group), aminoacridine (X or X' is an acridinyl group), and aminoquinoline (X or X' is a thiofuryl group). Examples of substituent on such compounds are halogens, nitro, lower alkyl, alkoxy, cyano, phenoxy, and amide (e.g., phenylaminocarbonyl) groups, and such phenoxy groups and amide groups may further contain additional substituent(s) such as halogen, lower alkyl, lower alkoxy, alkylaminosulfonyl, or nitrite.

An azo compound of the present invention may be obtained by coupling the diazonium compound [VII] or [VII'], obtained by diazotizing an aromatic amine with sodium nitrite or the like, to the above 2-hydroxynaphthalene-3,6-dicarboxylic acid or a derivative thereof (e.g., a carboxamide, carboxyureide, or ester).

Examples of such aromatic amine may include aniline, monoamino-fused polycyclic hydrocarbons such as α- or β-naphthylamine, monoaminoanthracene, monoaminoindene, and monoaminofluorenone, monoaminoindole, monoaminobenzothiophene, monoaminoquinoline, and monoaminocarbazole. These aromatic amines may have substituent(s) such as halogen, lower alkyl (in particular methyl), cyano, nitro, lower alkoxy, amide, sulfo, alkylaminosulfonyl, aminocarbonyl, phenoxy, alkoxycarbonyl, hydroxy, and benzoylamino groups.

Particularly preferred aromatic amines are anilines.

EXAMPLE 1

Synthesis of 1,4-bis{1'-(2",5"-dichlorophenylazo)-2'-hydroxy-6'-phenylaminocarbonyl-naphth-3'-yl-carbonylamino}phenylene

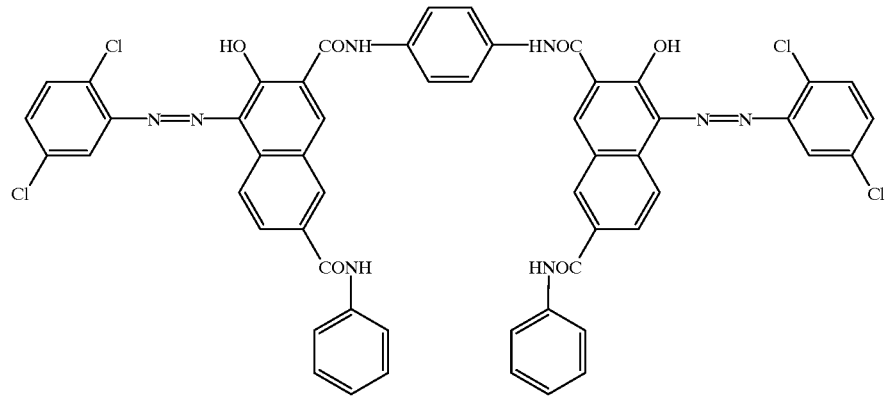

The process for preparing a diazonium compound from an amine is not specifically restricted. The standard method for diazotizing aromatic primary amines with sodium nitrite may be used.

The process in which the diazonium compound is further coupled with the above-described 2-hydroxynaphthalene-3, 6-dicarboxylic acid or a derivative thereof (e.g., a carboxamide, carboxyureide, or ester) may also be achieved by a conventional method.

The azo compounds of the present invention exhibit excellent water resistance, solvent resistance, chemical resistance, and heat resistance, and may be used in pigments, printing inks, paints, colorating agents for plastics, organic photoconductive materials, and the like.

The present invention is further described in reference to the following Examples. In Examples, "parts" or "%" means parts by weight or % by weight, respectively, unless specifically indicated.

As an amine component, 1.45 g of 2,5-dichloroaniline is suspended in 12.0 g of water, and 2.3 g of 36% hydrochloric acid is added thereto. While maintaining the temperature at 0–5° C., a solution of 0.7 g of sodium nitrite dissolved in 10 g of water is then added dropwise to achieve diazotization. Subsequently, 0.8 g of acetic acid, 0.15 g of Pearlite®, 0.15 g Carboraffin® added, and the mixture is filtered. The temperature is kept at not over 10° C. during this procedure. Separately, as a coupler component, 3.1 g of 1,4-bis(2'-hydroxy-6'-phenylaminocarbonyl-naphth-3'-yl-carbonylamino)phenylene is suspended in 124 g of N-methyl-2-pyrrolidone, a solution of 1.0 g of sodium hydroxide dissolved in 10 g of water added thereto, and kept at 15° C. following dissolution. To this, the clear diazo solution described above is added for 20 to 30 minutes to effect the coupling reaction. After stirring for 60 minutes, the reaction mixture is heated to 70° C., and further stirred for about 30 minutes. The reaction mixture was then gradually cooled, and suction-filtered at room temperature. The product was washed ultrasonically in each of methanol and water, and then dried under reduced pressure to yield 3.30 g of brownish red powder [1,4-bis{1'-(2",5"-dichlorophenylazo)-2'-hydroxy-6'-phenylaminocarbonyl-naphth-3'-yl-carbonylamino}phenylene] (melting/decomposing point: 396.6° C. (dec.))

Figure 1:
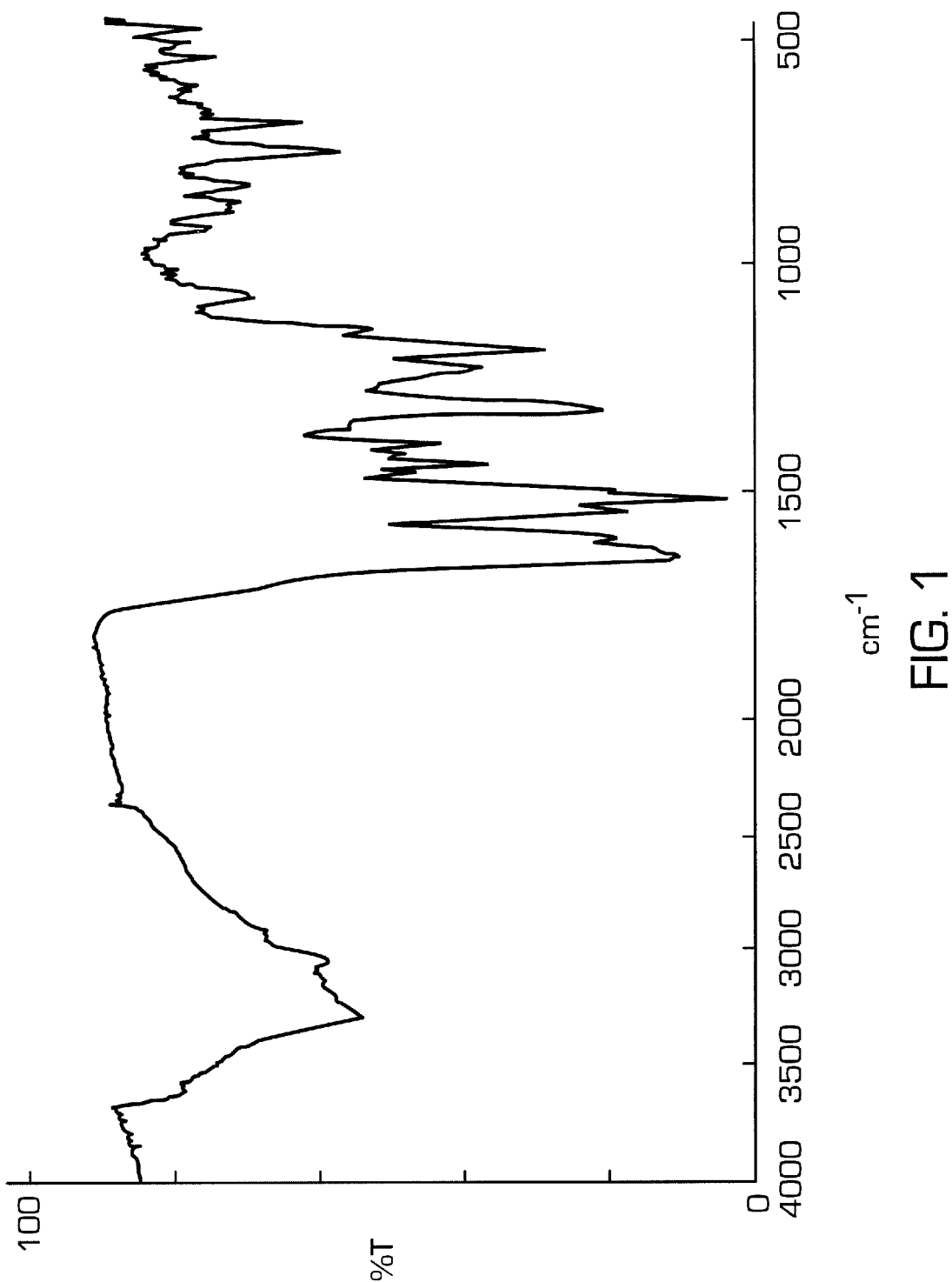
FIG. 1 is the infrared absorption spectrum of the compound obtained in Example 1.

The infrared absorption spectrum (diffuse reflection) of this product is shown in FIG. 1.

For the condensed azo compound obtained in Example 1, the properties are shown in Table 1, including water resistance, chemical resistance, solvent resistance, light resistance, and heat resistance.

Water resistance, chemical resistance, solvent resistance, light resistance, and heat resistance were measured as follows:

Experiment 1: Water Resistance

One part of the sample is added to 20 parts of water, and dispersed by sonicating for 20 minutes. After boiling for one minutes, the mixture is cooled, and filtered. The color of the filtrate was then observed, and evaluated according to the criteria A–E described below.

Experiment 2: Chemical Resistance

One part of the sample is added to 20 parts of 5% aqueous hydrochloric acid or sodium hydroxide, and dispersed by sonicating for 5 minutes. After filtration, the color of the filtrate was observed, and evaluated according to the criteria A–E described below.

Experiment 3: Solvent Resistance

One part of the sample is added to 20 parts of acetone, methanol, xylene, or ethyl acetate, and dispersed by sonicating 5 minutes. After filtration, the color of the filtrate was observed, and evaluated according to the following criteria A–E.

Evaluation of the above three items: A=not colored at all; B=colored quite slightly; C=colored slightly; D=colored; and E=colored remarkably.

Experiment 4: Light Resistance

1) One part of the sample, 0.7 parts of dioctyl phthalate, and 0.7 parts of castor oil are mulled in a Hoover-type muller (3×100 revolutions).

2) To one part of the mixture from 1), 10.0 parts of a hardening agent Beckozole® (ER-3653-60) and 0.1 part of manganese naphthenate are add, and kneaded with a spatula on a glass plate.

3) The sample obtained in 2) is laid on an iron plate to a thickness of 0.5 mil ($1.27 \times 10^{-5}$ m) using an applicator, and then heated at 145° C. for 30 minutes in a forced-air dryer to obtain a test piece of baking finish.

4) A half of the test piece of 3) is masked, and then irradiated in a feather meter (Shimadzu Corporation; Suntester® XF-180/xenon lamp) for 100 hours. The masked and unmasked areas are each subjected to colorimetry, and the light resistance is evaluated on the basis of the color difference ΔE between the two areas.

| | |
|---|---|
| ΔE < 2 | A |
| ΔE = 2–3 | B |
| ΔE = 3–5 | C |
| ΔE = 5–8 | D |
| ΔE > 8 | E |

Experiment 5: Heat Resistance

1) To 100 parts of a composition consisting of 100 parts of soft polyvinyl chloride, 50 parts of dioctyl phthalate, 2 parts of tin maleate, 0.4 parts of calcium stearate, and 0.6 parts of barium stearate, one part of the sample is added, mulled for 5 minutes at 140° C. in a twin-roll mill, and then compressed at 100 kgf/cm$^2$ to obtain a test sheet of 1 mm thickness.

2) The test sheet obtained in 1) is cut into 30 mm x 30 mm pieces.

3) The test pieces of 2) are left in an incubator at 170° C. for 60 minutes. The test pieces were subjected to colorimetry before and after the heating, and the heat resistance was evaluated on the basis of the color difference ΔE.

| | |
|---|---|
| ΔE < 2 | A |
| ΔE = 2–3 | B |
| ΔE = 3–5 | C |
| ΔE = 5–8 | D |
| ΔE > 8 | E |

TABLE 1

| Example No. | Structural formula of condensed azo compound |
|---|---|
| 1 | [Structural formula of condensed azo compound] |

| Example No. | Color | Decomposing point | Water resistance | Chemical resistance HCl | Chemical resistance NaOH | Solvent resistance, acetone | Solvent resistance, methanol | Solvent resistance, xylene | Solvent resistance, ethyl acetate | Light resistance | Heat resistance |
|---|---|---|---|---|---|---|---|---|---|---|---|
| 1 | brownish red | 396.6 C. ° | A | A | A | A | A | A | A | A | A |

EXAMPLE 2

Synthesis of 1,4-bis{1'-(2",5"-dichlorophenylazo)-2'-hydroxy-3'-phenylaminocarbonyl-naphth-6'-yl-carbonylamino}phenylene

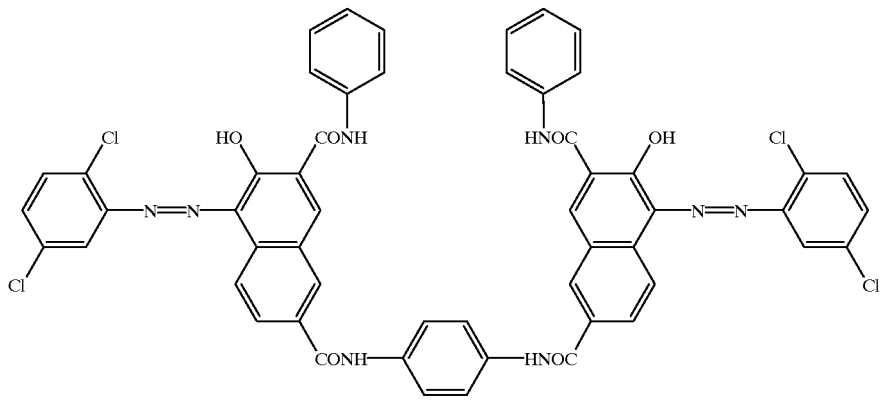

In the same manner as Example 1, except that as the coupler component, 3.1 g of 1,4-bis(2'-hydroxy-3'-phenylaminocarbonyl-naphth-6'-yl-carbonylamino)phenylene was substituted for 1,4-bis(2'-hydroxy-6'-phenylaminocarbonyl-naphth-3'-yl-carbonylamino)phenylene used in Example 1, 3.28 g of brownish red powder [1,4-bis{1'-(2'',5''-dichlorophenylazo)-2'-hydroxy-3'-phenylaminocarbonyl-naphth-6'-yl-carbonylamino}phenylene] was obtained (melting/decomposing point: 368.6° C. (dec.)).

EXAMPLE 3

Synthesis of 1-{1'-(2'',5''-dichlorophenylazo)-2'-hydroxy-3'-phenylaminocarbonyl-naphth-6'-yl-carbonylamino}-4-{1'-(2'',5''-dichlorophenylazo)-2'-hydroxy-6'-phenylaminocarbonylnaphth-3'-yl-carbonlamino}phenylene phenylaminocarbonyl-naphth-6'-yl-carbonylamino)-4-(2'-hydroxy-6'-phenylaminocarbonyl-naphth-3'-yl-carbonylamino)phenylene was substituted for 1,4-bis(2'-hydroxy-6'-phenylaminocarbonyl-naphth-3'-yl-carbonylamino)phenylene used in Example 1, 2.67 g of brownish red powder [1-{1'-(2'',5''-dichlorophenylazo)-2'-hydroxy-3'-phenylaminocarbonyl-naphth-6'-yl-carbonylamino}-4-{1'-(2',5'-dichlorophenylazo)-2'-hydroxy-6'-phenylaminocarbonyl-naphth-3'-yl-carbonylamino} phenylene] was obtained (melting/decomposing point: 356.1° C. (dec.)).

EXAMPLE 4

Synthesis of 1-{1'-(2'',5''-dichlorophenylazo)-2'-hydroxy-3'-phenylaminocarbonyl-naphth-6'-yl-carbonylamino}-3-{1'-(2'',5''-dichlorophenylazo)-2'-hydroxy-6'-

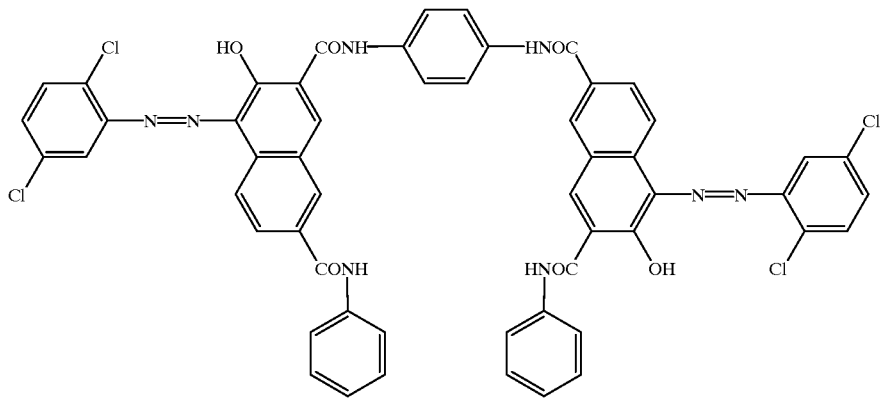

In the same manner as Example 1, except that as the coupler component, 3.1 g of 1-(2'-hydroxy-3'-phenylaminocarbonyl-naphth-3'-yl-carbonylamino}phenylene

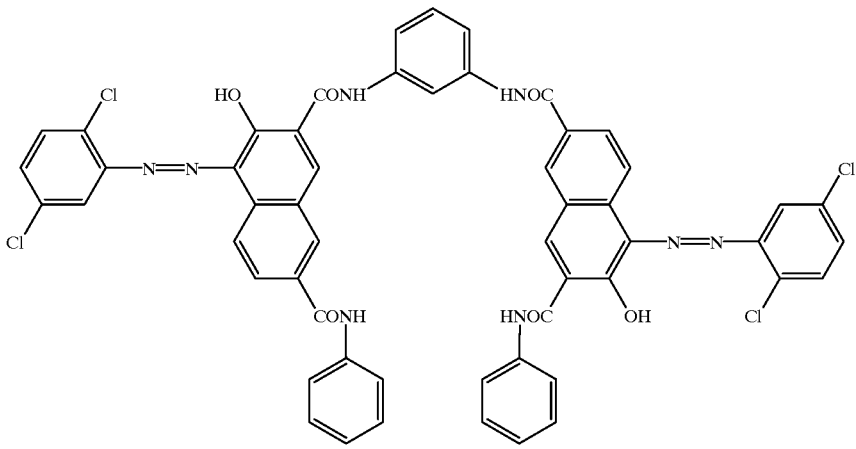

In the same manner as Example 1, except that as the coupler component, 3.1 g of 1-(2'-hydroxy-3'-phenylaminocarbonyl-naphth-6'-yl-carbonylamino)-3-(2'-hydroxy-6'-phenylaminocarbonyl-naphth-3'-yl-carbonylamino)phenylene was substituted for 1,4-bis(2'-hydroxy-6'-phenylaminocarbonyl-naphth-3'-yl-carbonylamino)phenylene used in Example 1, 3.50 g of brownish red powder [1-{1'-(2",5"-dichlorophenylazo)-2'-hydroxy-3'-phenylaminocarbonyl-naphth-6'-yl-carbonylamino}-3-{1'-(2",5"-dichlorophenylazo)-2'-hydroxy-6'-phenylaminocarbonyl-naphth-3'-yl-carbonylamino}phenylene] was obtained (melting/decomposing point: 339.6° C. (dec.)).

EXAMPLE 5

Synthesis of bis[4-{-1'-(2",5"-dichlorophenylazo)-2'-hydroxy-6'-phenylaminocarbonyl-naphth-3'-yl-carbonylamino}phenyl]methane In the same manner as Example 1, exceptthat as the coupler component, 3.5 g of bis{4-(2'-hydroxy-6'-phenylaminocarbonyl-naphth-3'-yl-carbonylamino) phenyl}methane was substituted for 1,4-bis(2'-hydroxy-6'-phenylaminocarbonyl-naphth-3'-yl-carbonylamino) phenylene used in Example 1, 2.32 g of yellowish red powder [bis[4-{1'-(2",5"-dichlorophenylazo)-2'-hydroxy-6'-phenylamino carbonyl-naphth-3'-yl-carbonylamino}phenyl] methane] was obtained (melting/decomposing point: 353.0° C. (dec.)).

EXAMPLE 6

Synthesis of bis[4-{1-(2",5"-dichlorophenylazo)-2'-hydroxy-3'-phenylaminocarbonyl-naphth-6'-yl-carbonylamino}phenyl]methane

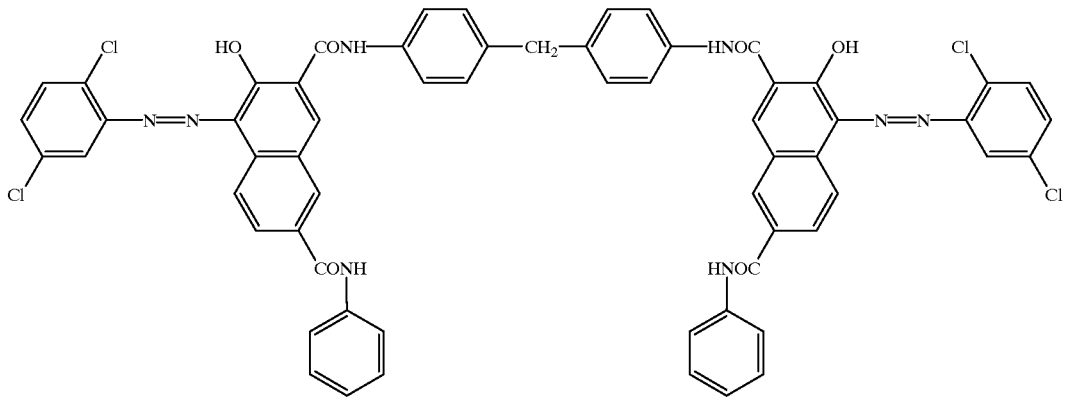

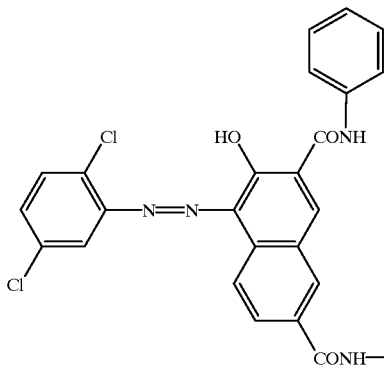

In the same manner as Example 1, except that as the coupler component, 3.5 g of bis{4-(2'-hydroxy-3'-phenylaminocarbonyl-naphth-6'-yl-carbonylamino)phenyl}methane was substituted for 1,4-bis(2'-hydroxy-6'-phenylaminocarbonyl-naphth-3'-yl-carbonylamino)phenylene used in Example 1, 1.54 g of bluish red powder [bis[4-{1'-(2",5"-dichlorophenylazo)-2'-hydroxy-3'-phenylaminocarbonyl-naphth-6'-yl-carbonylamino}phenyl]methane] was obtained (melting/decomposing point: 332.0° C. (dec.)).

In the same manner as Example 1, except that as the coupler component, 3.5 g of bis{(4-(2'-hydroxy-6'-phenylaminocarbonyl-naphth-3'-yl-carbonylamino)phenyl} ether was substituted for 1,4-bis(2'-hydroxy-6'-phenylaminocarbonyl-naphth-3'-yl-carbonylamino)phenylene used in Example 1, 1.61 g of yellowish red powder [bis[4-{1'-(2",5"-dichlorophenylazo)-2'-hydroxy-6'-phenylaminocarbonyl-naphth-3'-yl-carbonylamino}phenyl] ether] was obtained (melting/decomposing point: 368.1° C. (dec.)).

EXAMPLE 7

Synthesis of bis[4-{1'-(2",5"-dichlorophenylazo)-2'-hydroxy-6'-phenylaminocarbonyl-naphth-3'-yl-carbonylamino}phenyl] ether

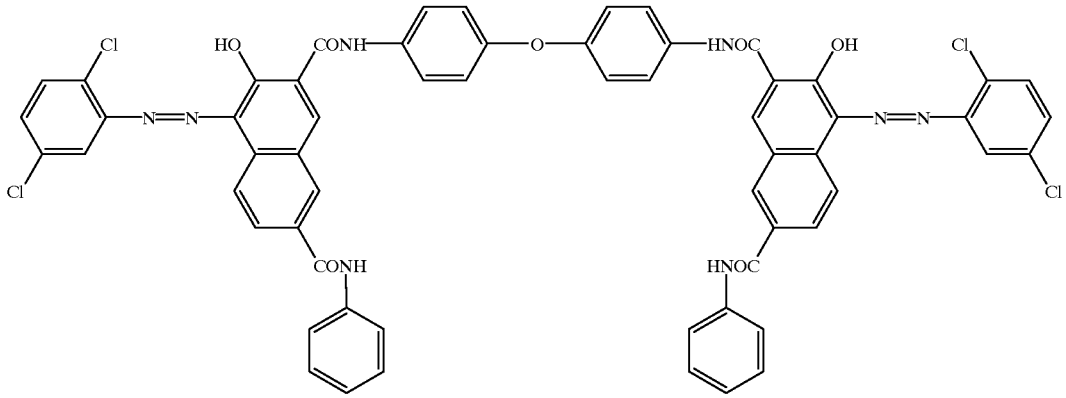

EXAMPLES 8–28

In the same manner as Example 1, except that the amines and couplers indicated in Table 3 were used as the amine and coupler components, respectively, azo compounds were synthesized. The melting/decomposing point for each azo compound synthesized is shown in Table 2.

TABLE 2

| Example No. | Structural formula of condensed azo compound | Color | Decomposition point |
|---|---|---|---|
| 8 | | yellowish red | 337.0° C. |
| 9 | | dark bluish red | 380.4° C. |

TABLE 2-continued

| Example No. | Structural formula of condensed azo compound | Color | Decomposition point |
|---|---|---|---|
| 10 | | yellowish red | 329.7° C. |
| 11 | | bluish red | 310.9° C. |

TABLE 2-continued

| Example No. | Structural formula of condensed azo compound | Color | Decomposition point |
|---|---|---|---|
| 12 | | dark brown | 348.8° C. |
| 13 | | brownish red | 331.3° C. |

TABLE 2-continued
| Example No. | Structural formula of condensed azo compound | Color | Decomposition point |
|---|---|---|---|
| 14 | 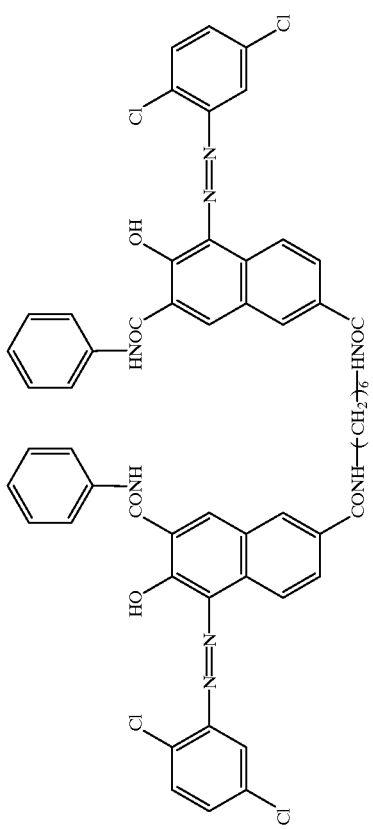 | yellowish red | 308.7° C. |
| 15 | 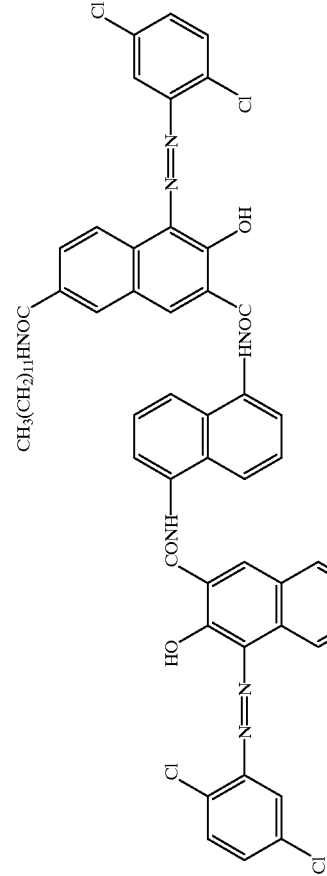 | dark brownish red | 299.9° C. |

TABLE 2-continued

Structural formula of condensed azo compound

| Example No. | Color | Decomposition point |
|---|---|---|
| 16 | reddish brown | 408.7° C. |
| 17 | brown | 402.5° C. |
| 18 | dark brownish red | 360.3° C. |

TABLE 2-continued

| Example No. | Structural formula of condensed azo compound | Color | Decomposition point |
| --- | --- | --- | --- |
| 19 | | dark brownish red | 358.1° C. |
| 20 | | brownish red | 334.5° C. |

TABLE 2-continued

Structural formula of condensed azo compound

| Example No. | Color | Decomposition point |
|---|---|---|
| 21 | brownish red | 354.4° C. |
| 22 | dark reddish brown | 329.5° C. |
| 23 | dark yellowish red | 332.1° C. |

TABLE 2-continued

Structural formula of condensed azo compound

| Example No. | Color | Decomposition point |
|---|---|---|
| 24 | dark brownish red | 327.8° C. |
| 25 | dark brownish red | 293.5° C. |

TABLE 2-continued

Structural formula of condensed azo compound

| Example No. | Color | Decomposition point |
|---|---|---|
| 26 | dark brown | 326.3° C. |
| 27 | dark purplish red | 315.3° C. |

TABLE 2-continued
| Example No. | Structural formula of condensed azo compound | Color | Decomposition point |
|---|---|---|---|
| 28 | 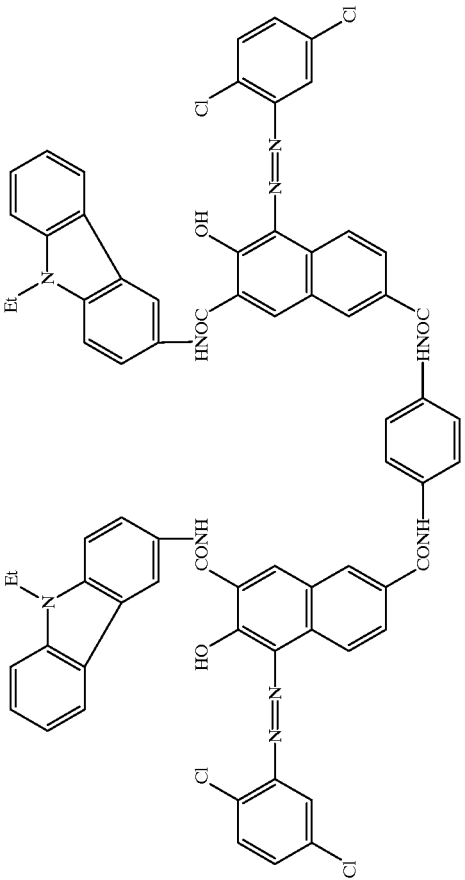 | dark bluish red | 331.9° C. |

TABLE 3

| Example No. | Amine compound | Coupler component |
|---|---|---|
| 8 | (aniline) | (bis-naphthol bis-phenylamide coupler, para-phenylenediamine linker) |
| 9 | (3-amino-4-methoxy-N-phenylbenzamide) | (bis-naphthol bis-phenylamide coupler, para-phenylenediamine linker) |
| 10 | (2-chloro-5-trifluoromethylaniline) | (bis-naphthol bis-phenylamide coupler, meta-phenylenediamine linker) |

TABLE 3-continued

| Example No. | Amine compound | Coupler component |
| --- | --- | --- |
| 11 | 2-amino ethyl benzoate (COOEt, NH₂ on benzene) | (complex bis-naphthol bisamide structure with p-phenylenediamine linker and two benzimidazolone end groups) |
| 12 | 2,5-dichloroaniline | (complex bis-naphthol bisamide structure with p-phenylenediamine linker; one end benzimidazolone, other end phenyl) |
| 13 | 2,5-dichloroaniline | (bis-naphthol bisamide structure with ethylenediamine linker and two phenyl end groups) |

TABLE 3-continued

| Example No. | Amine compound | Coupler component |
| --- | --- | --- |
| 14 | 2,5-dichloroaniline | bis-naphthol coupler with CONH-(CH₂)₆-HNOC linker and phenyl amide groups |
| 15 | 2,5-dichloroaniline | bis-naphthol coupler linked through naphthalene with CH₃(CH₂)₁₁HNOC substituents |
| 16 | 2,5-dichloroaniline | bis-naphthol coupler linked through 1,4-phenylene with COOCH₃ substituents |
| 17 | 2,4,5-trichloroaniline | bis-naphthol coupler linked through 1,4-phenylene with COOCH₃ substituents |

TABLE 3-continued

| Example No. | Amine compound | Coupler component |
| --- | --- | --- |
| 18 | 2,5-dichloroaniline | (structure with two hydroxynaphthalene-carboxamide units linked via naphthalene, bearing CH$_3$(CH$_2$)$_7$OOC– and –COO(CH$_2$)$_7$CH$_3$ groups) |
| 19 | 2,5-dichloroaniline | (structure with two hydroxynaphthalene-carboxamide units linked via naphthalene, bearing CH$_3$(CH$_2$)$_{15}$OOC– and –COO(CH$_2$)$_{15}$CH$_3$ groups) |
| 20 | 2,5-dichloroaniline | (bis-hydroxynaphthalene-carboxanilide linked through –CONH–C$_6$H$_4$–N=N–C$_6$H$_4$–HNOC–) |
| 21 | 2,5-dichloroaniline | (bis-hydroxynaphthalene-carboxanilide linked through –CONH–C$_6$H$_4$–CH=C(CN)–C$_6$H$_4$–HNOC–) |

TABLE 3-continued
| Example No. | Amine compound | Coupler component |
|---|---|---|
| 22 | 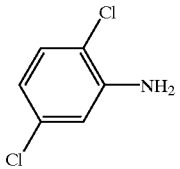 | 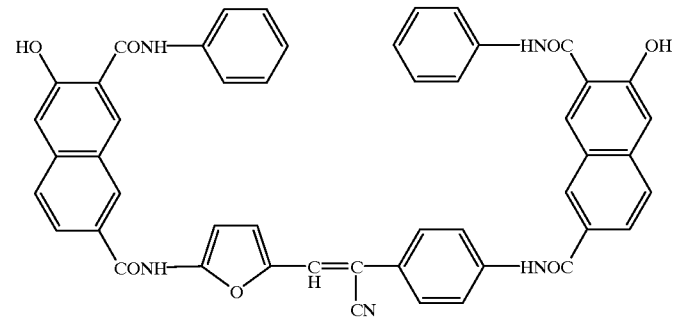 |
| 23 | 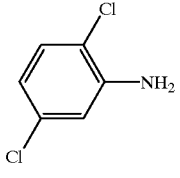 | 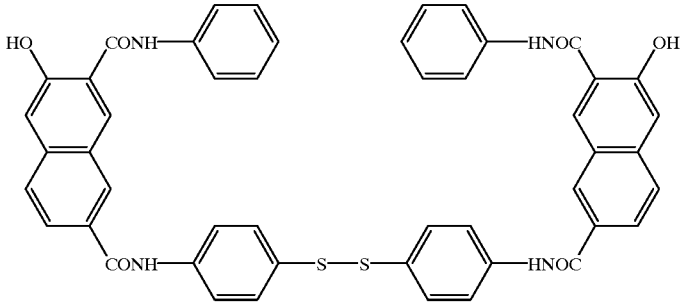 |
| 24 | 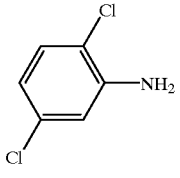 | 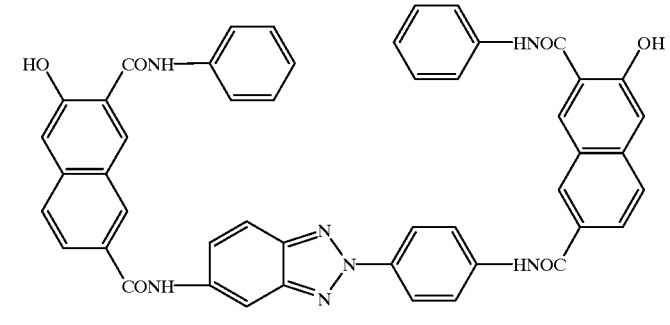 |
| 25 | 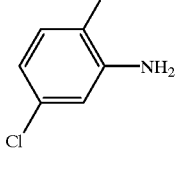 | 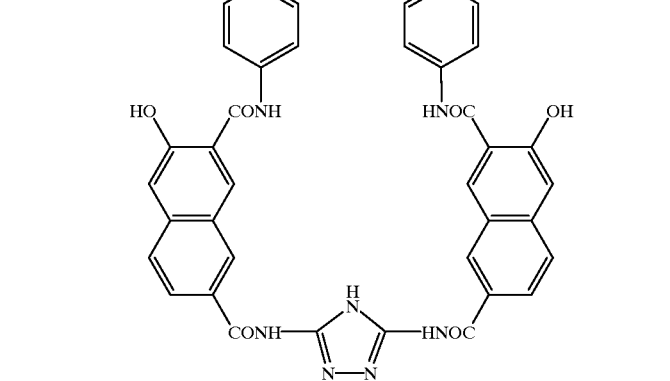 |

TABLE 3-continued

| Example No. | Amine compound | Coupler component |
|---|---|---|
| 26 | 2,5-dichloroaniline | (structure) |
| 27 | 3-amino-4-methoxy-N,N-diethylbenzenesulfonamide | (structure) |
| 28 | 2,5-dichloroaniline | (structure) |

EXAMPLE 29

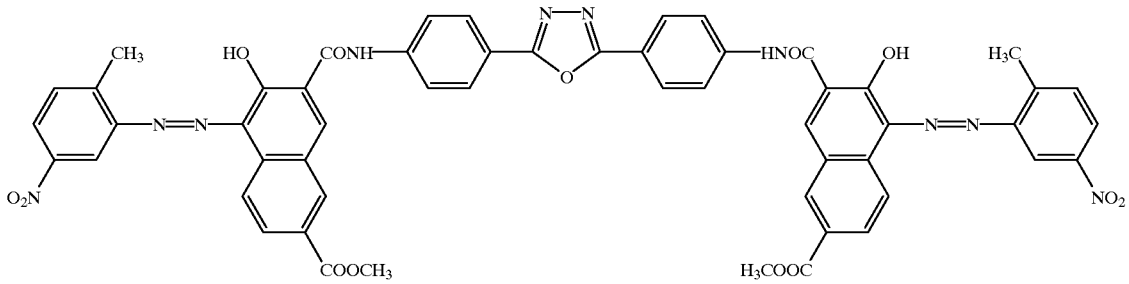

In 100 g of N,N-dimethylformamide, 1.25 g of 2-hydroxy-3-hydroxycarbonyl-6-methoxycarbonylnaphthalene and 2.2 g of a diazonium borofluoride prepared from 4-nitrotoluidine in the usual manner are dissolved. To this, a solution of 7.4 g of sodium acetate dissolved in 20 g of water is slowly added, while maintaining the temperature at 10–15° C. After stirring for about 2 hours, the precipitate is recovered by filtration. The precipitate is thoroughly washed with water and methanol, and then dried. In 20 g of tetrahydrofuran, 1.03 g of monoazo compound thus obtained is suspended, and 0.75 g of thionyl chloride is added thereto. After adding a small amount of additional N,N-dimethylformamide, the temperature is raised to 60–70° C. The reaction is allowed to proceed sufficiently with stirring for about 15 hours, and the excess of thionyl chloride is then evaporated. To this, a solution of 0.33 g of 2,5-di(4'-aminophenyl)-3,4-oxadiazole dissolved in 20 g of N-methyl-2-pyrrolidone is added. After stirring at 70–80° C. for about 20 hours, 10 g of methanol is added. The precipitate was recovered by filtration, washed thoroughly with water and methanol, and then dried to yield 1.21 g of yellowish red powder which contained the intended product as a major component (melting/decomposing point: 292.2° C. (dec.)).

At this stage, the thickness of the film was about 0.5 μm. Onto the carrier generation layer thus obtained, a solution consisting of one part of N-ethylcarbazole-3-aldehyde diphenylhydrazone and one part of polycarbonate resin (TEIJIN Chemicals Co., Panlite K-1285) dissolved in 20 parts of 1,2-dichloroethane was applied so that, when dried, a 20 μm thick film would be obtained to form an carrier transport layer. In this way, a photosensitive material for electrophotography consisting of two layers was obtained.

The half-exposure ($E_{1/2}$) as a sensitivity of photosensitive material was measured for the above photosensitive material using an electrostatic copy paper tester (K. K. Kawaguchi Denki Seisakusho Model EPA-8100). The material was firstly electrified by corona discharge at −5.0 kV in darkness, and then exposed to white light at an illumination of 20 luxes in order to determine the exposure dose required to decay the surface potential to the half of the initial value.

The half-exposure ($E_{1/2}$) thus determined was 6.8 lux·sec. And the surface potential after sufficient exposure (residual potential) (after exposed to 200 lux·sec) was −1 V.

In addition, using the azo compounds obtained in Examples 22, 27, and 28, photosensitive materials for electrophotography were prepared as described above, and measured for their half-exposures ($E_{12}$'s) and surface potentials (residual potentials). The half-exposure ($E_{1/2}$) and surface potential (residual potential) for each compounds are shown in Table 4.

EXAMPLE 30

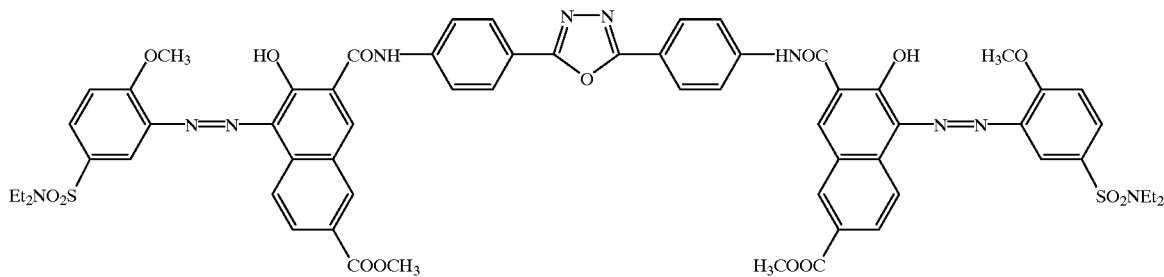

In the same manner as Example 29, except that 2-methoxy-5-diethylaminosulfonylaniline was substituted for 4-nitrotoluidine to obtain the corresponding diazonium borofluoride, 1.08 g of dark bluish red powder which contained the intended product as a major component was obtained (melting/decomposing point: 248.4° C. (melt), 301.7° C. (dec.)).

Experiment 6: Photoconductive Properties

One part of the azo compound obtained in Example 26 was dispersed with one part of a poly(vinyl butyral) (Sekisui Chemical Co., S-LEC BH-3) and 10 parts of cyclohexanone using ball mill. The dispersed azo compound was applied onto an aluminum plate using bar applicator, and then dried.

TABLE 4

| Example No. | Structural formula of condensed azo compound | Half-exposure, $E_{1/2}$ (lux·sec) | Residual potential, $V_r$ |
|---|---|---|---|
| 22 | (structure) | 7.4 | −2 V |
| 27 | (structure) | 7.4 | −2 V |

TABLE 4-continued

| Example No. | Structural formula of condensed azo compound | Half-exposure, $E_{1/2}$ (lux · sec) | Residual potential, $V_r$ |
|---|---|---|---|
| 28 | | 8.6 | −2 V |

EXAMPLE 31

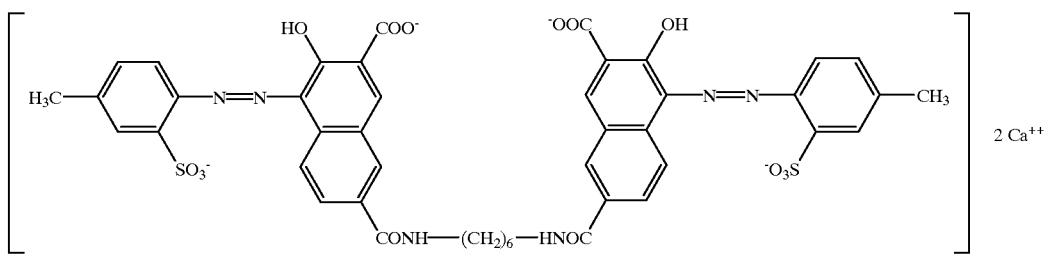

In 50 g of water, 1.89 g of 4-aminotoluene-3-sulfonic acid (4B-Acid) is dispersed, and dissolved by adding 2.57 g of 35% hydrochloric acid. Then, diazotization is conducted by adding dropwise a solution of 0.84 g of sodium nitrite dissolved in 5 g of water, while maintaining the temperature at 0° C. Separately, 2.72 g of 1,6-bis(2'-hydroxy-3'-hydroxynaphth-6ylcarbonylamino)hexane is suspended in 100g of water, and 7.0 g of 10% sodium hydroxide and 4.0 g of 5% aqueous solution of rosin are added thereto, dissolved, and then kept at 13 (±2) °C. To this, the above-described diazo solution is added dropwise over about 30 minutes, and stirred for additional 90 minutes. The reaction solution is adjusted to pH 9.0–9.5, and then converted into a lake by adding dropwise a solution of 2.20 g of calcium chloride dihydrate dissolved in 20 g of water. After 30 minutes, the mixture is heated to 70° C., kept for about 30 minutes at that temperature, and gradually cooled to room temperature. To this mixture, 200 g of water is added, pH adjusted to 6.0–6.5, and then the precipitate recovered by filtration. The product was washed with water, and dried to yield 4.12 g of dark red powder (melting/decomposing point: 501.6° C. (dec.)).

EXAMPLE 32

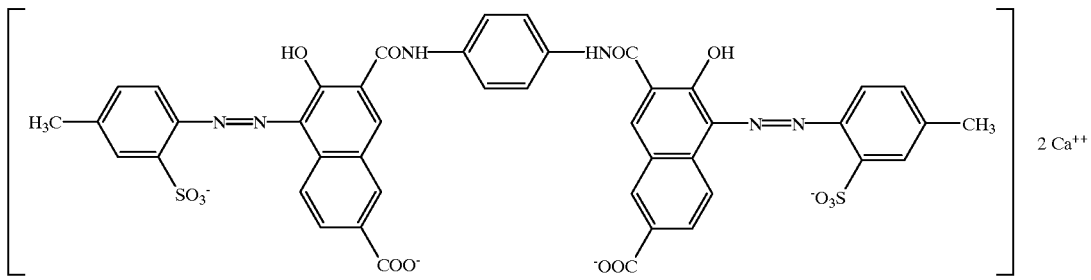

In the same manner as Example 31, except that 2.68 g of 1,4-bis(2'-hydroxy-6'-hydroxynaphth-3'-ylcarbonylamino) phenylene was substituted for 1,6-bis(2'-hydroxy-3'-hydroxynaphth-6'-ylcarbonylamino)hexane used in Example 31, 3.92 g of dark bluish red powder was obtained (melting/decomposing point: 472.8° C. (dec.)).

Experiment 7: Color Data as Printing Inks

With the azo compounds obtained in Examples 31 and 32, printing inks were prepared according to JIS K5101, and developed. The color data are shown in Table 5. As such color data, the dominant wave-length $\lambda$d, the excitation purity Pe, and the brightness Y as described in JIS Z8701 are shown.

TABLE 5

|  | Dominant wavelength $\lambda$d | Excitation purity Pe | Brightness Y |
| --- | --- | --- | --- |
| Example 31 | 627 nm | 43.3% | 11.8% |
| Example 32 | 636 nm | 28.7% | 15.4% |

EXAMPLE 33–37

In the same manner as Example 1, except that the amines and couplers indicated in Table 7 were used as the amine and coupler components, respectively, azo compounds were synthesized. The melting/decomposing point for each azo compound synthesized is shown in Table 6.

TABLE 6

| Example No. | Structural formula of condensed azo compound | Color | Decomposing point |
|---|---|---|---|
| 33 | | somewhat dark brownish red | 288.9° C. |
| 34 | | somewhat dark yellowish red | 304.6° C. |

TABLE 6-continued
| Example No. | Structural formula of condensed azo compound | Color | Decomposing point |
|---|---|---|---|
| 35 | 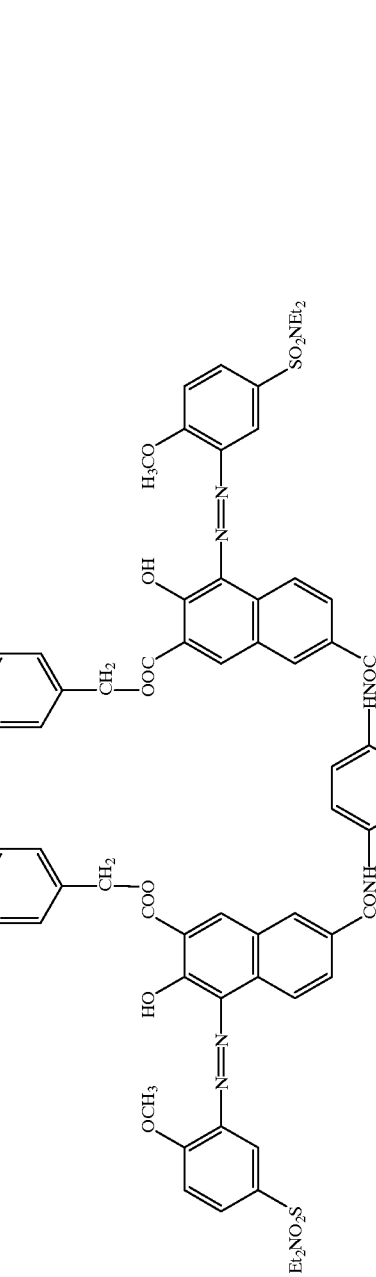 | dark brownish red | 284.6° C. |
| 36 | 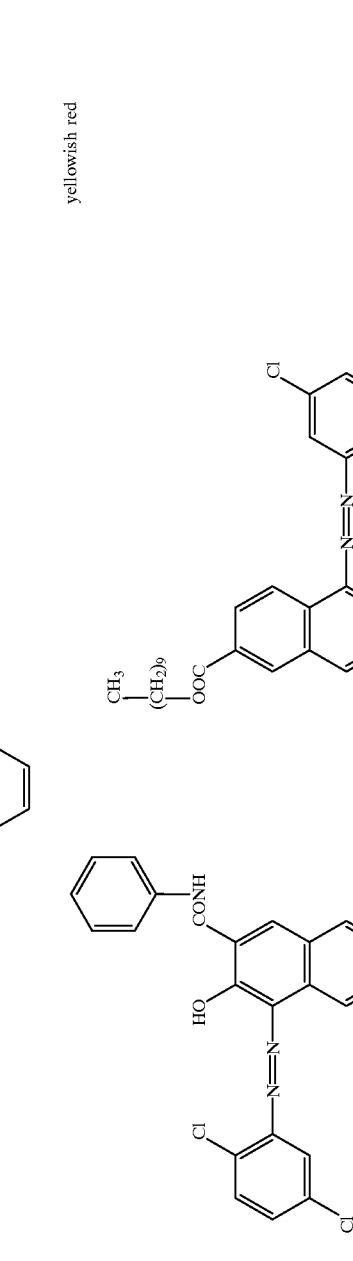 | yellowish red | 339.8° C. |

TABLE 6-continued
| Example No. | Structural formula of condensed azo compound | Color | Decomposing point |
|---|---|---|---|
| 37 | 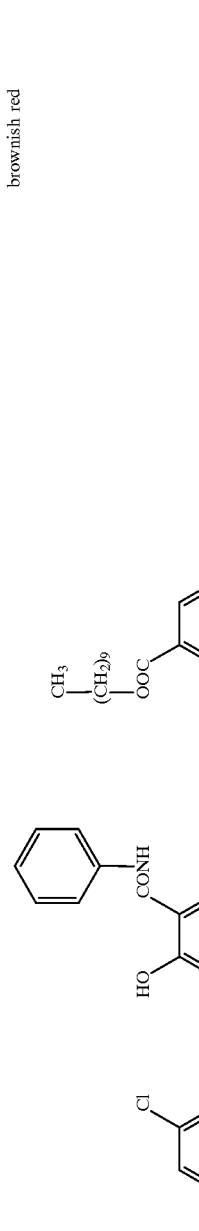 | brownish red | 295.6° C. |

TABLE 7
| Example No. | Amine component | Coupler component |
|---|---|---|
| 33 | 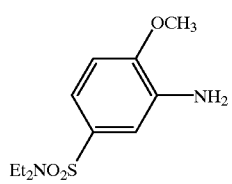 | 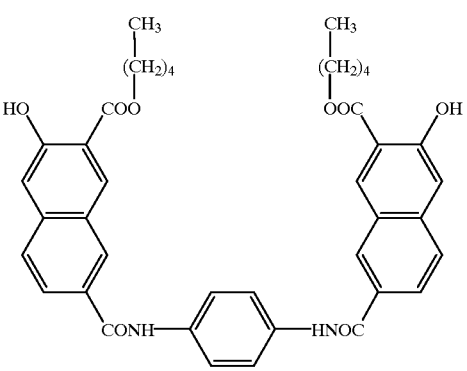 |
| 34 | 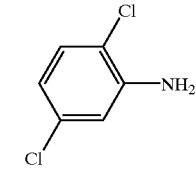 | 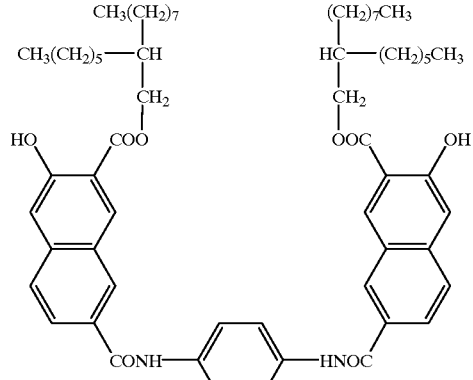 |
| 35 | 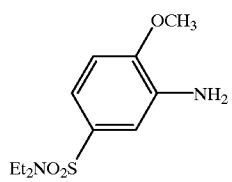 | 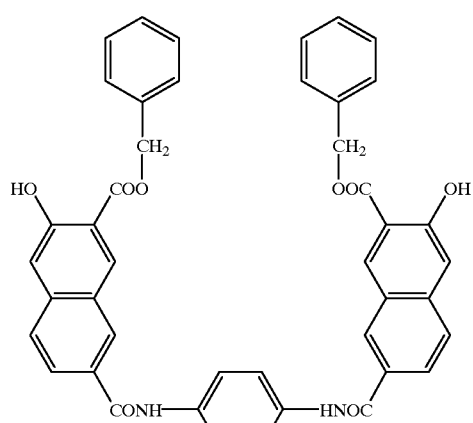 |

TABLE 7-continued

| Example No. | Amine component | Coupler component |
|---|---|---|
| 36 | 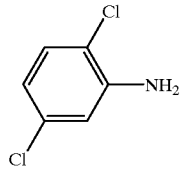 | 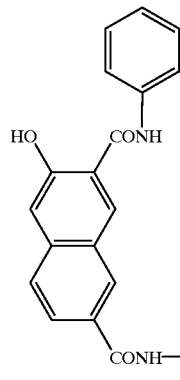 |
| 37 | 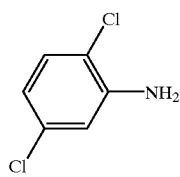 | 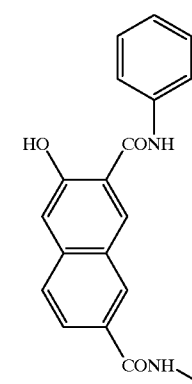 |

EXAMPLE 38

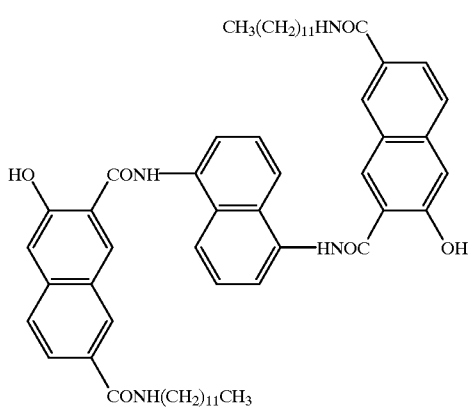

An acid chloride is prepared in the usual manner from 7.39 g of 2-hydroxy-6-hydroxycarbonyl-3-methoxycarbonylnaphthalene, and a solution of 6.82 g of n-dodecylamine dissolved in 25 g of N-methyl-2-pyrrolidone and 13 g of xylene is added thereto dropwise at 80° C. After allowing to proceed the reaction for about 18 hours, the reaction is ice-cooled, and the precipitate is recovered by filtration. The precipitate (10.48 g) washed with acetone is dissolved in 100 g of N,N-dimethylformamide at 60° C., and a solution of 3.2 g of sodium carbonate dissolved in 100 g of water and 30 g of methanol is added. The reaction is allowed to proceed for 2 hours at 80° C., and 100 g of water is further added following removal of insoluble matter. The solution is adjusted to pH 2. The precipitate formed is recovered by filtration, washed with warm water and methanol, and dried. The crystal (1.02 g) thus obtained is suspended in 22.16 g of tetrahydrofuran, added 0.35 g of thionyl chloride, and reacted for about 15 hours in ice bath. After evaporating the remaining thionyl chloride, a solution of 0.13 g of 1,5-diaminonaphthalene dissolved in 7.35 g of N-methyl-2-pyrrolidone is added. After allowing to proceed the reaction for about 40 hours, the precipitate was recovered by filtration, washed with water and methanol, and dried to yield 0.15 g of grayish blue powder (melting/decomposing point: 371.6° C. (dec.)).

Figure 2:
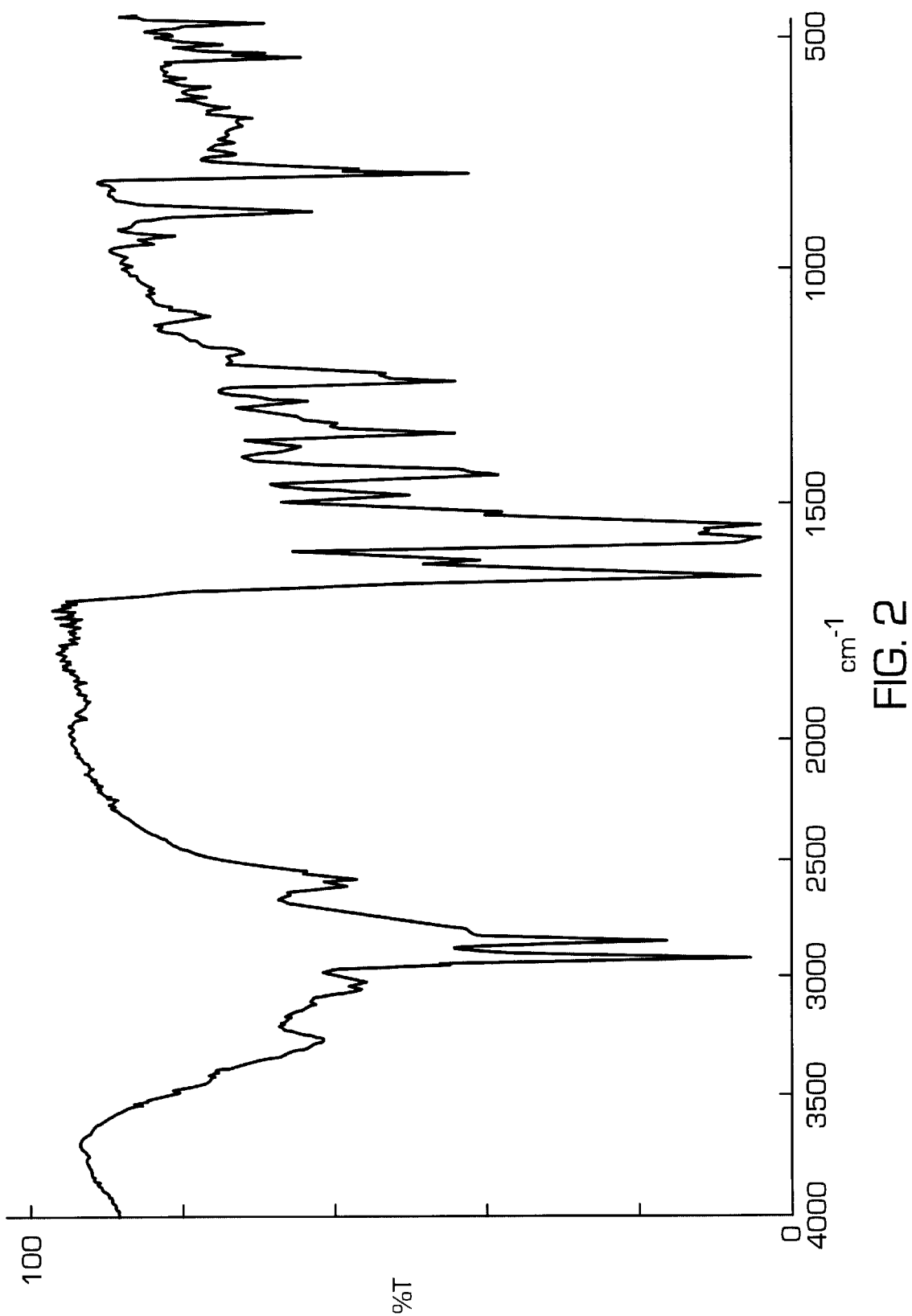
FIG. 2 is the infrared absorption spectrum of the compound obtained in Example 38.

The infrared absorption spectrum (KBr) for this product is shown in FIG. 2.

EXAMPLE 39

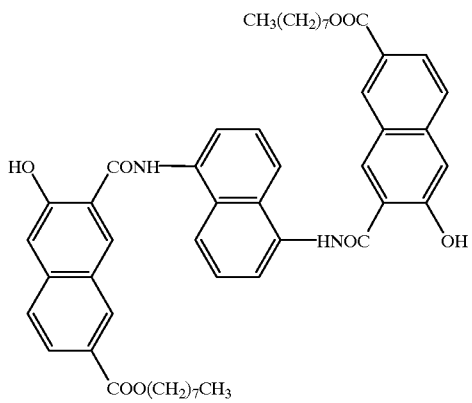

In the same manner as Example 38, except that n-octyl alcohol was substituted for n-dodecylamine used in Example 38, 0.38 g of skin colored powder was obtained (melting/decomposing point: 95.2° C. (melt), 320.8° C. (dec.)).

Figure 3:
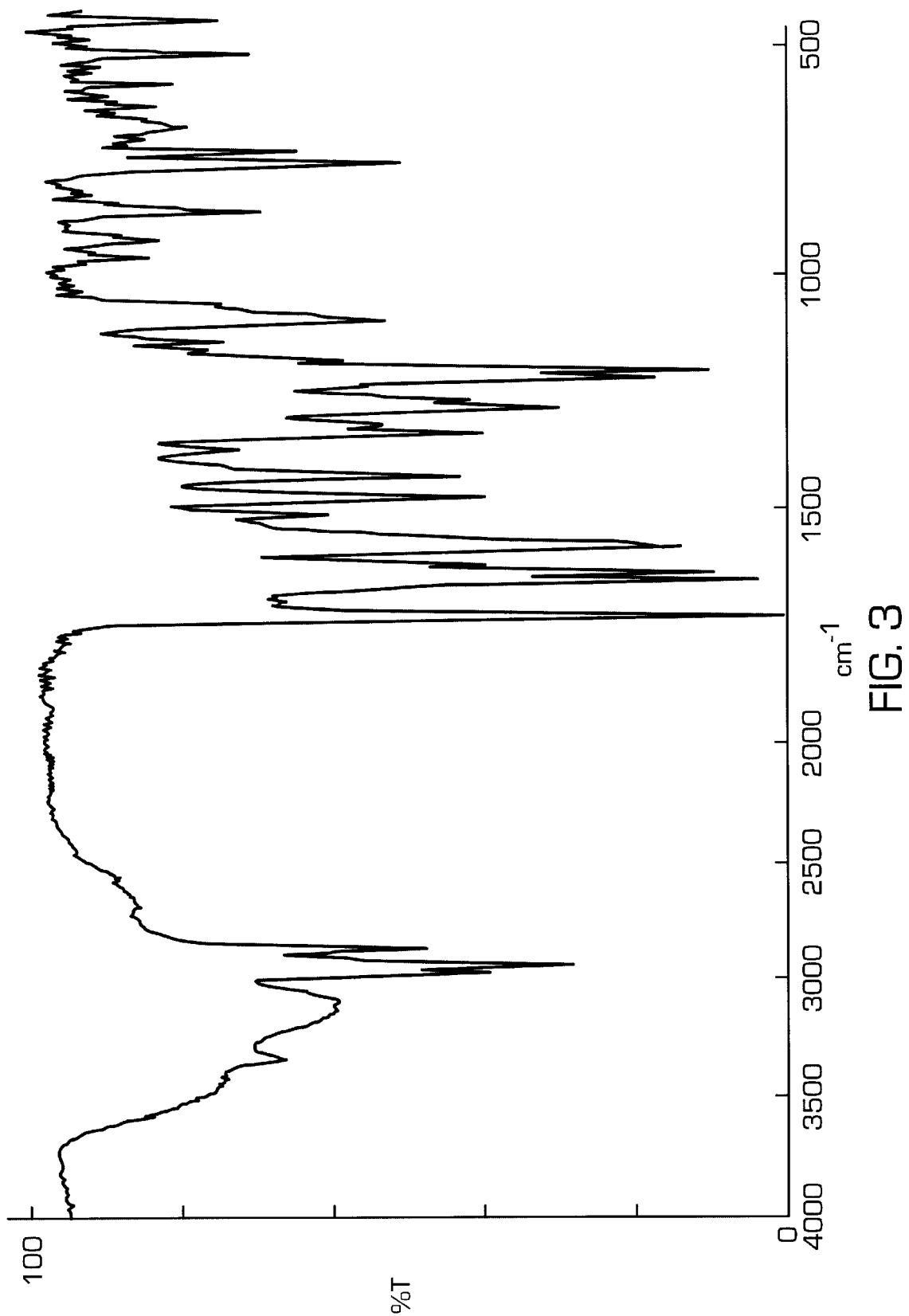
FIG. 3 is the infrared absorption spectrum of the compound obtained in Example 39.

The infrared absorption spectrum (KBr) of this product is shown in FIG. 3.

EXAMPLE 40

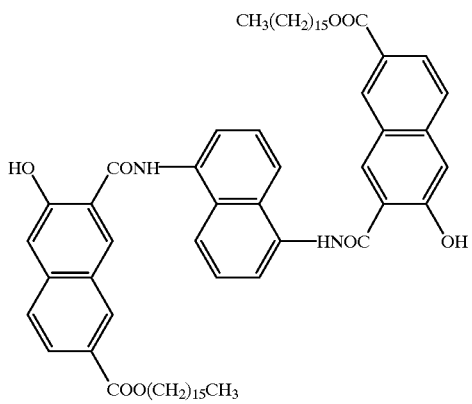

In the same manner as Example 38, except that 1-hexadecanol was substituted for n-dodecylamine used in Example 38, 0.61 g of skin colored powder was obtained (melting/decomposing point: 127.5° C. (melt), 329.5° C. (dec.)).

Figure 4:
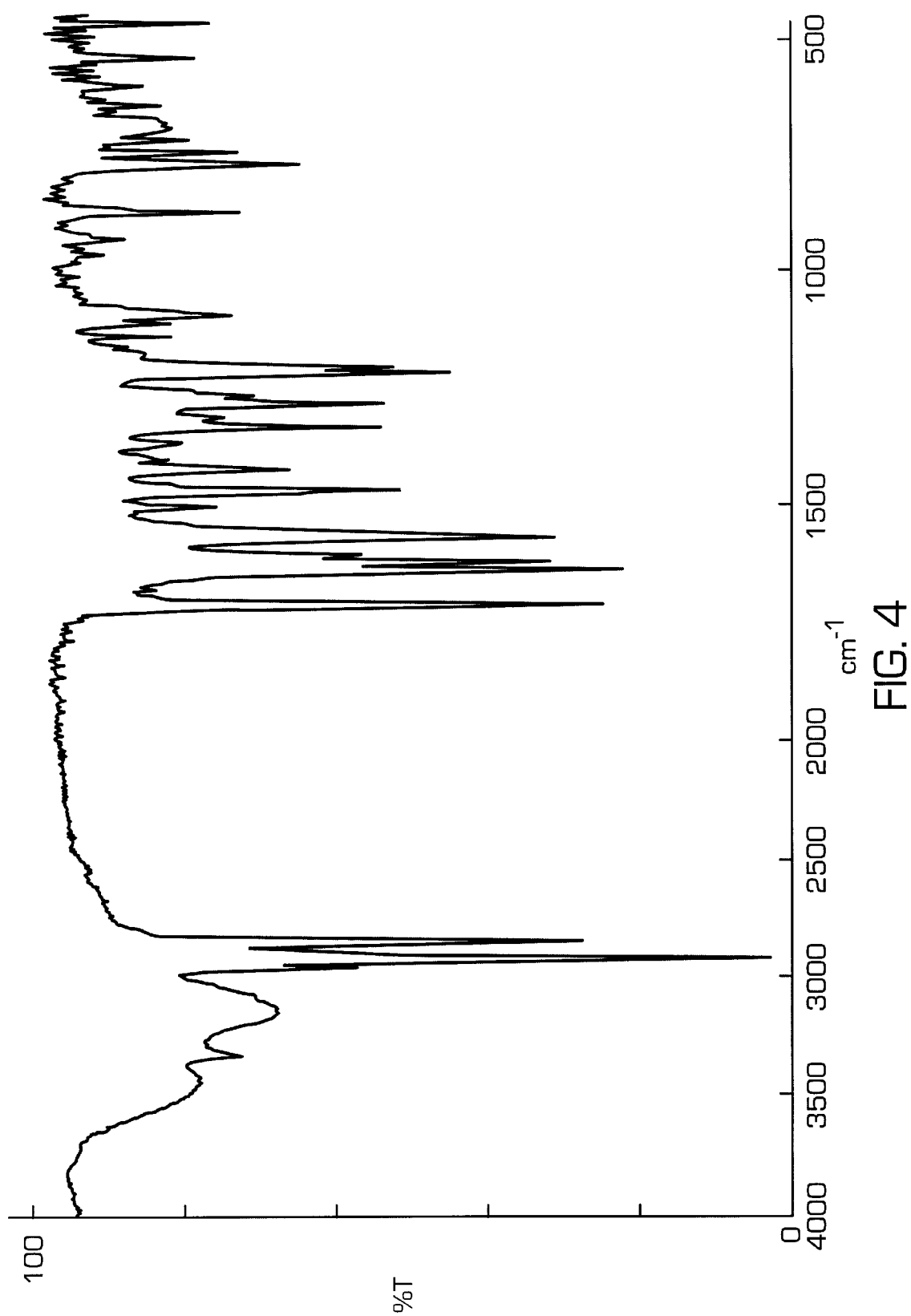
FIG. 4 is the infrared absorption spectrum of the compound obtained in Example 40.

The infrared absorption spectrum (KBr) of this product is shown in FIG. 4.

EXAMPLE 41

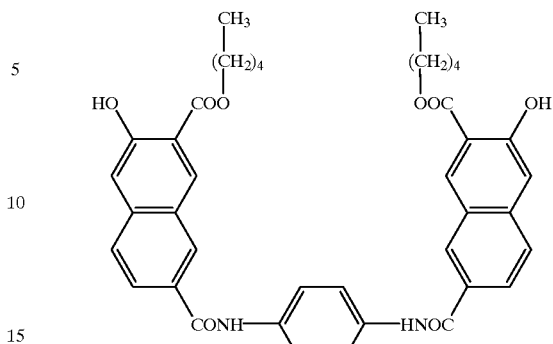

In 60g of tetrahydrofuran, 8.2 g of 2-hydroxy-6-hydroxycarbonyl-3-methoxycarbonylnaphthalene is suspended. To this suspension, 7.8 g of thionyl chloride and a small amount of N,N-dimethylformamide are added, and heated to 50° C. After allowing to proceed the reaction for about 3 hours, the solvent and other volatile are evaporated. To the residue, a solution of 1.62 g of p-phenylenediamine dissolved in 13 g of tetrahydrofuran and 3.5 g of N-methyl-2-pyrrolidone is added, and reacted for about 20 hours under reflux. The precipitate was recovered by filtration, and washed with methanol. The solid thus obtained is suspended in 200 g of methanol, 50 g of 24% sodium hydroxide added, and reacted at 50° C. for 6 hours. To this, 200 g of water is added, pH adjusted to 2, and the precipitate recovered by filtration. The precipitate was washed with warm water and methanol, and then dried to yield 2.6 g of 1,4-bis(2-hydroxy-3-methoxycarbonylnaphth-6-ylcarbonylamino)phenylene.

Furthermore, an acid chloride is prepared from the above compound in the usual manner, and a solution of 2.6 g of n-amyl alcohol dissolved in 20 g of N-methyl-2-pyrrolidone is added thereto. After allowing to proceed the reaction at 80° C. for 18 hours, 50 g of methanol is added, and the precipitate is recovered by filtration. The precipitate was washed thoroughly with methanol, and dried to yield 0.68 g of off-white powder (melting/decomposing point: 300.4° C. (dec.)).

Figure 5:
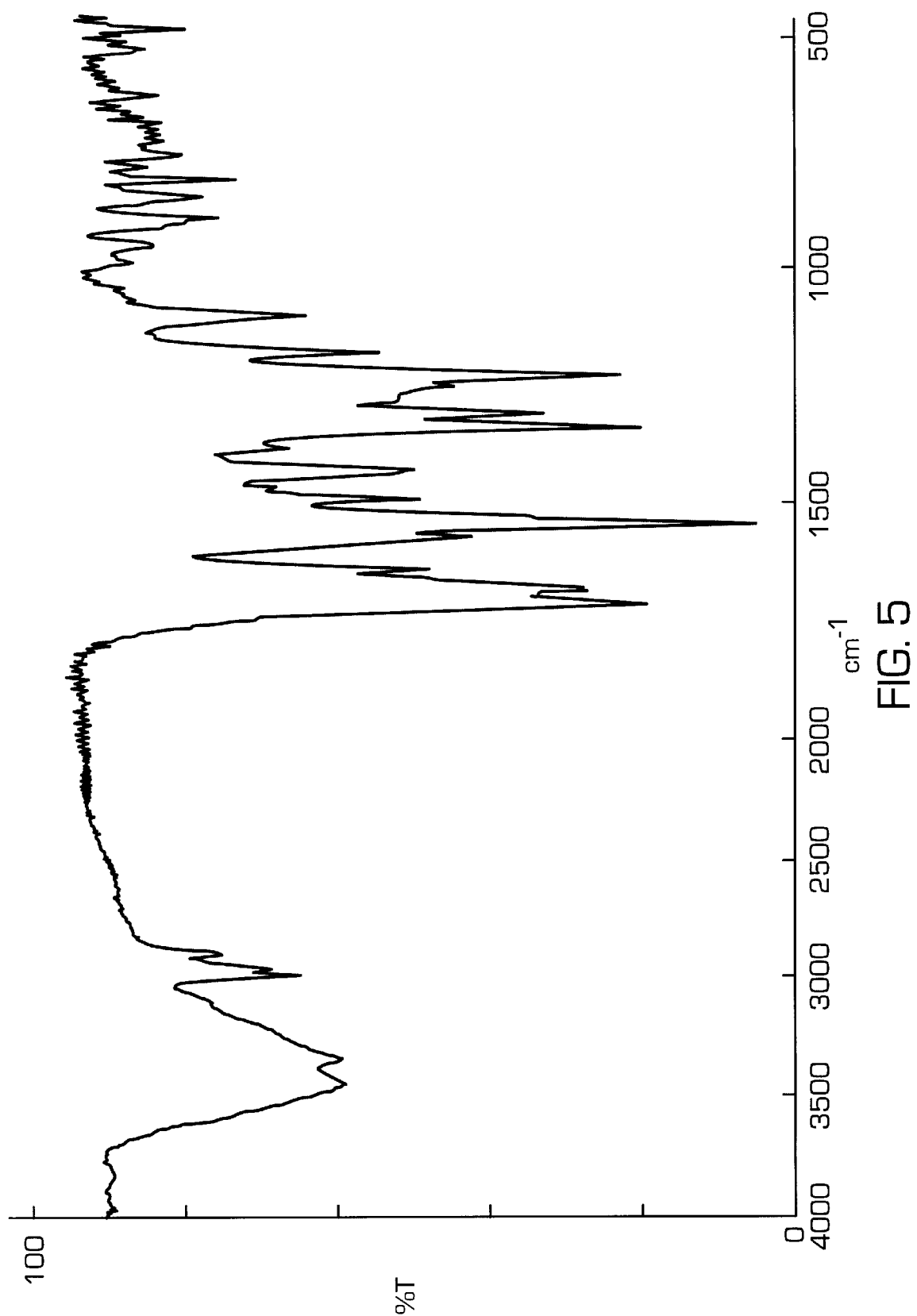
FIG. 5 is the infrared absorption spectrum of the compound obtained in Example 41.

The infrared absorption spectrum (KBr) of this product is shown in FIG. 5.

EXAMPLE 42

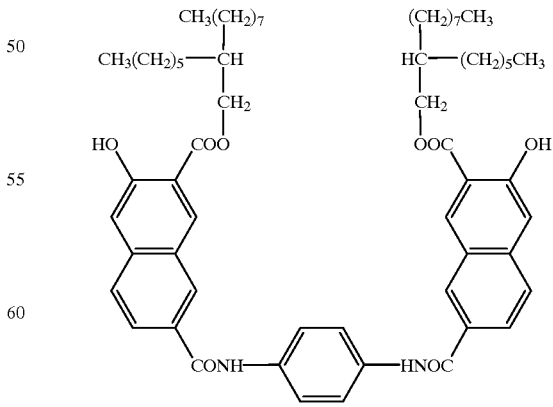

In the same manner as Example 41, except that 7.3 g of 2-hexyldecanol was substituted for n-amyl alcohol used in Example 41, 0.83 g of off-white powder was obtained (melting/decomposing point: 225.8° C. (melt)).

Figure 6:
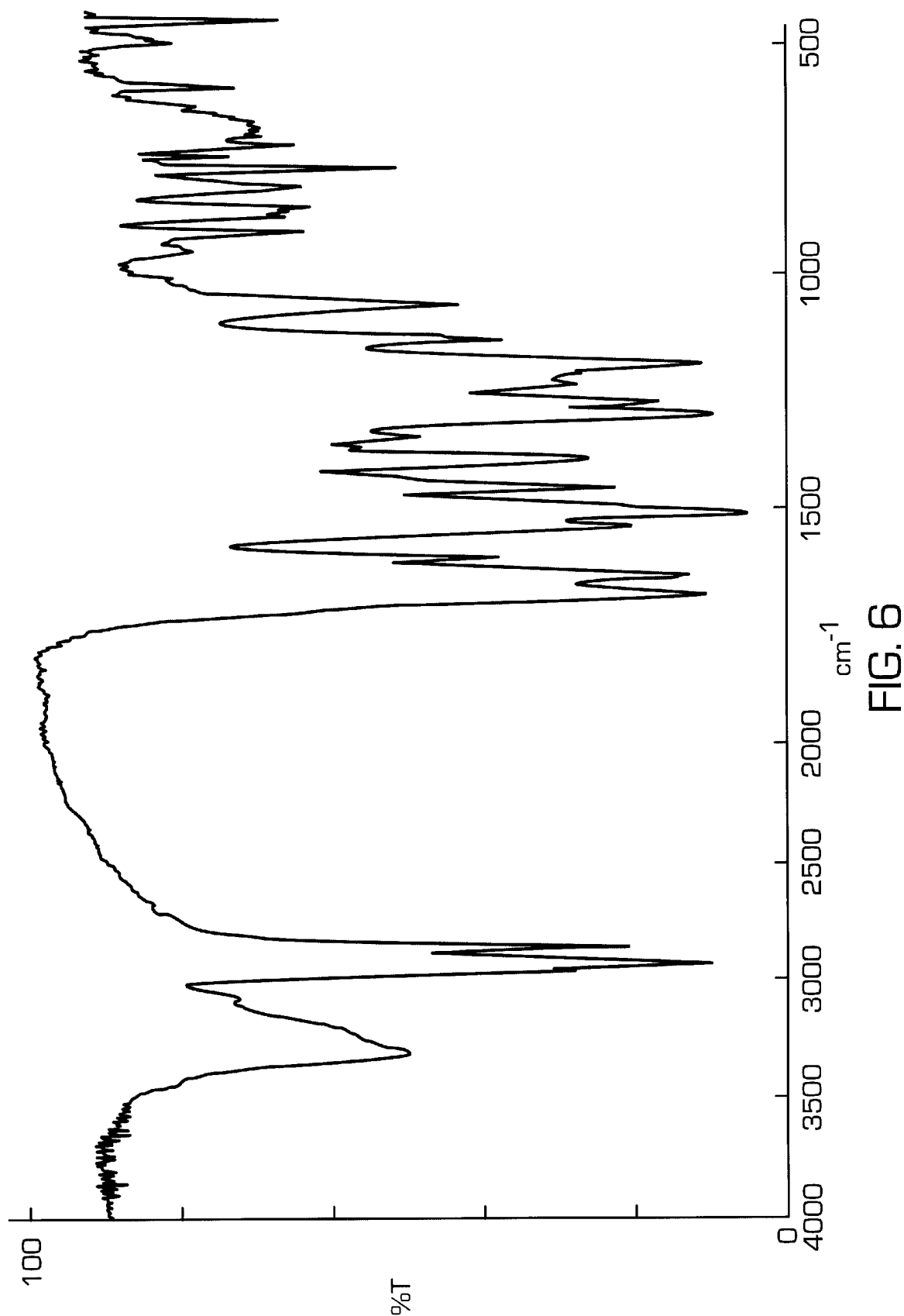
FIG. 6 is the infrared absorption spectrum of the compound obtained in Example 42.

The infrared absorption spectrum (KBr) of this product is shown in FIG. 6.

EXAMPLE 43

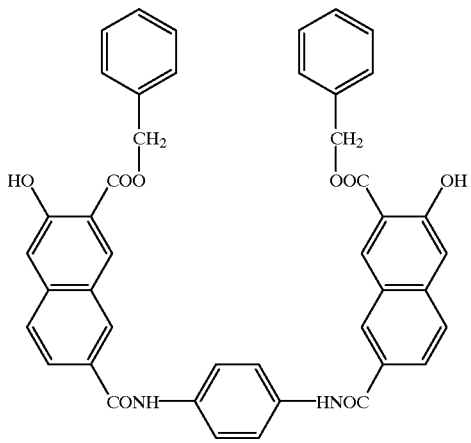

In the same manner as Example 41, except that 3.2 g of benzyl alcohol was substituted for n-amyl alcohol used in Example 41, 0.76 g of off-white powder was obtained (melting/decomposing point: 283.0° C. (melt)).

Figure 7:
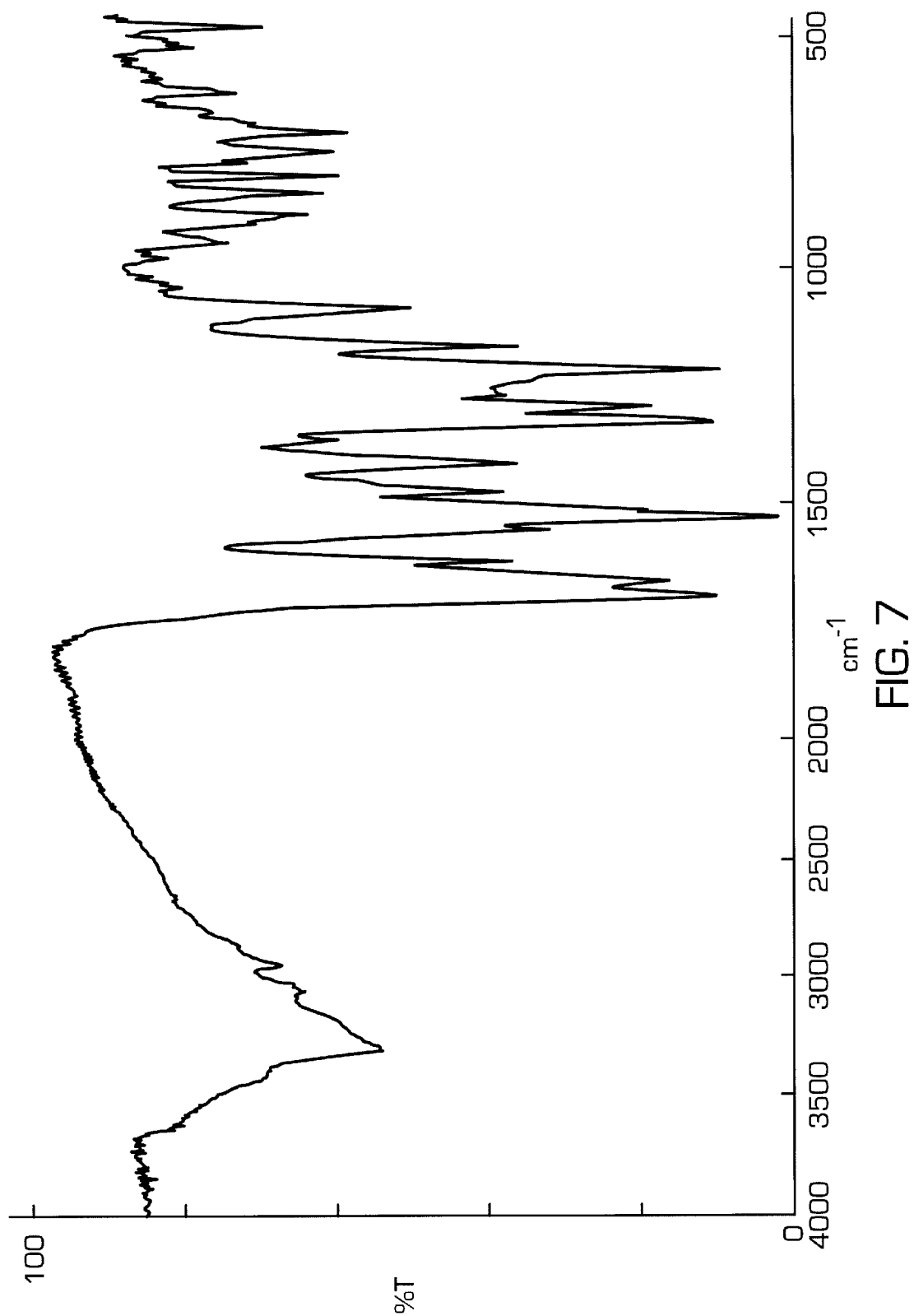
FIG. 7 is the infrared absorption spectrum of the compound obtained in Example 43.

The infrared absorption spectrum (KBr) of this product is shown in FIG. 7.

EXMAPLE 44

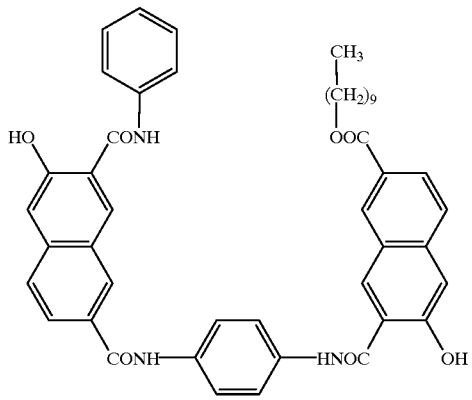

In 10.0 g of tetrahyrofuran, 1.00 g of 2-hydroxy-6-hydroxycarbonyl-3-methoxycarbonylnaphthalene is suspended. To this, 0.94 g of thionyl chloride and a small amount of N,N-dimethylformamide are added, and heated to 50° C. After allowing to proceed the reaction for about 3 hours, the solvent and other volatile are evaporated. To the residue, a solution of 1.27 g of n-decanol dissolved in 10.0 g of tetrahydrofuran is added, and reacted for about 20 hours under reflux. After evaporating the solvent, 15.0 g of N,N-dimethylformamide, 15.0 g of methanol, and 180.0 g of 5% aqueous sodium hydrogencarbonate are added, and reacted for 20 hours at 60° C. After removing insoluble matter, the pH of the reaction mixture is adjusted to pH 2 at 50° C., and the precipitate is recovered by filtration. The product was washed with warm water and methanol, and dried to yield 1.33 g of 2-hydroxy-3-hydroxycarbonyl-6-decyloxycarbonylnaphthalene as a white-yellow powder (melting/decomposing point: 269.2° C. (dec.)).

Furthermore, an acid chloride is prepared from the above compound in the usual manner, and a solution of 1.00 g of 2-hydroxy-6-(4'-aminophenylaminocarbonyl)-3-phenylaminocarbonylnaphthalene dissolved in 60.0 g of N-methyl-2-pyrrolidone is added thereto. After allowing to proceed the reaction at 80° C. for 18 hours, 200 g of methanol is added, and the precipitate is recovered by filtration. The precipitate was washed thoroughly with methanol, and dried to yield 0.99 g of off-white powder (melting/decomposing point: 296.8° C. (dec.)).

Figure 8:
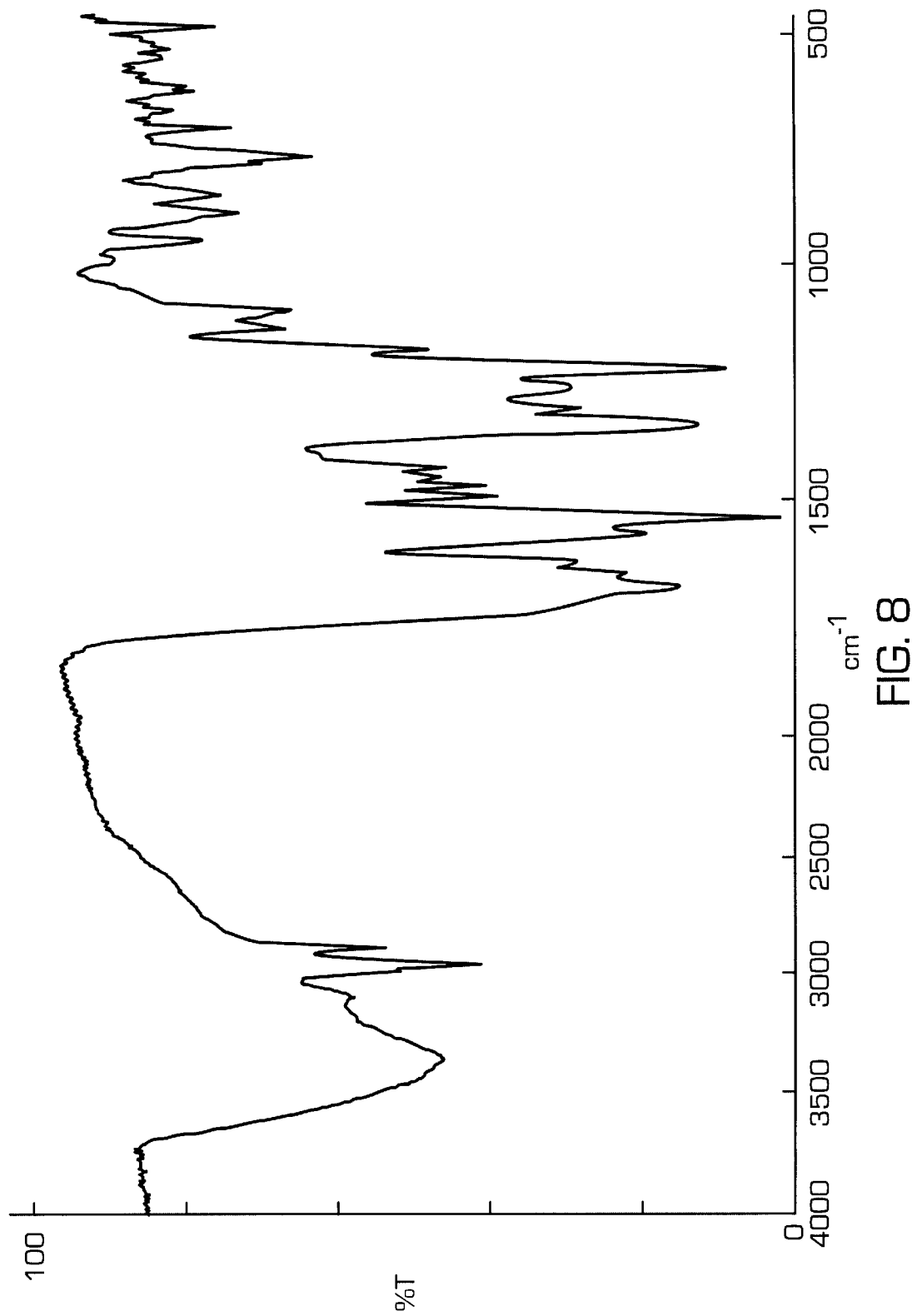
FIG. 8 is the infrared absorption spectrum of the compound obtained in Example 44.

The infrared absorption spectrum (KBr) of this product is shown in FIG. 8.

EXAMPLE 45

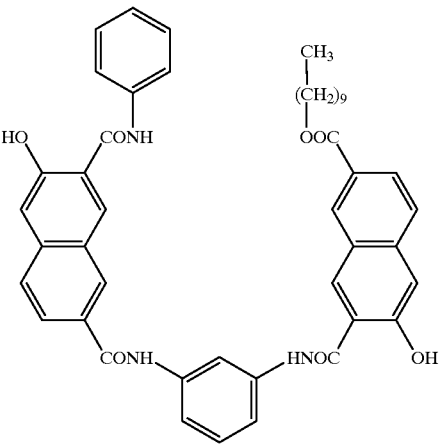

In the same manner as Example 44, except that 1.00 g of 2-hydroxy-6-(3'-aminophenylaminocarbonyl)-3-phenylaminocarbonylnaphthalene was substituted for 2-hydroxy-6-(4'-aminophenylcarbonyl)-3-phenylaminocarbonylnaphthalene used in Example 44, 0.93 g of tan powder was obtained (melting/decomposing point: 311.2° C. (dec.)).

Figure 9:
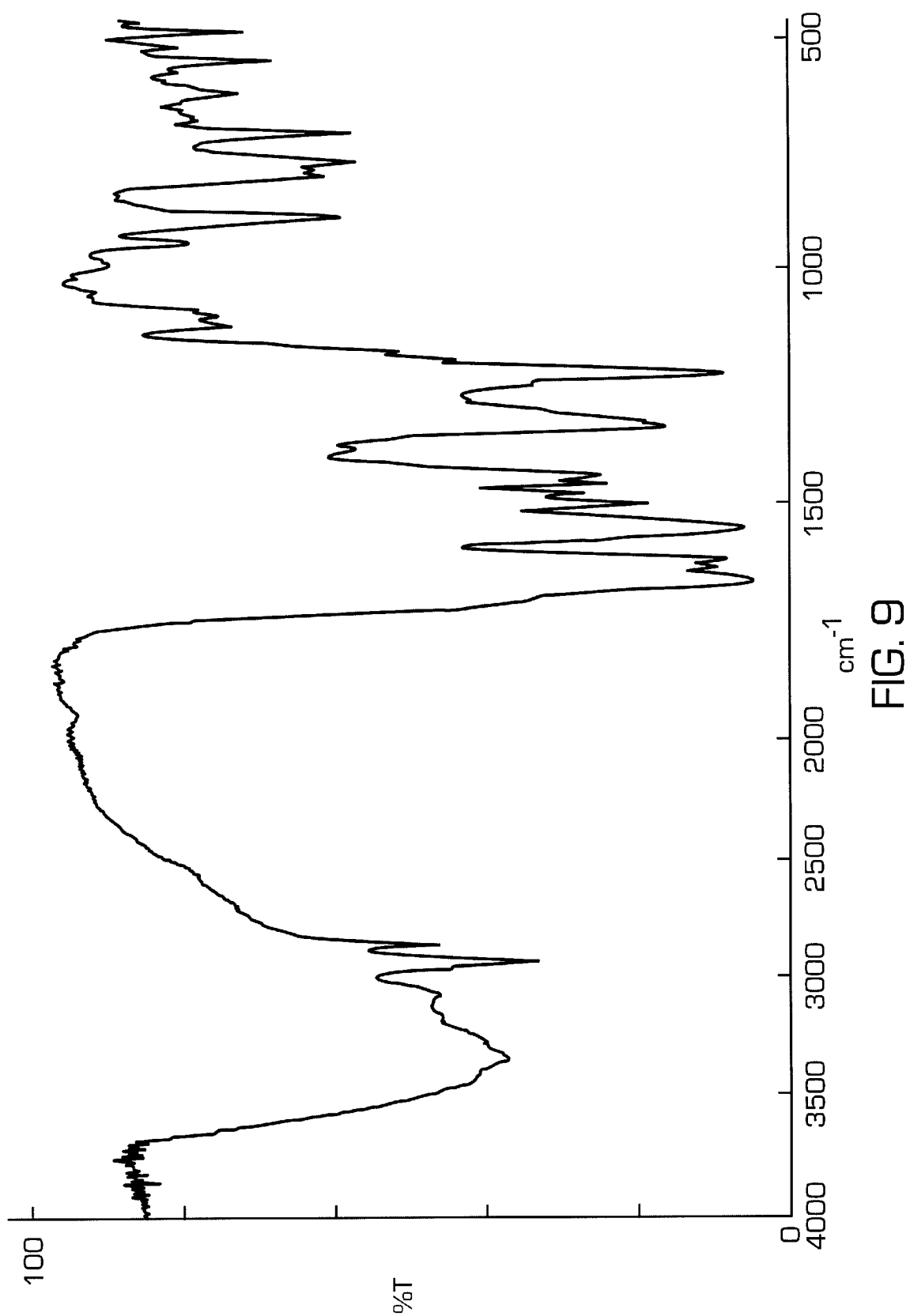
FIG. 9 is the infrared absorption spectrum of the compound obtained in Example 45.

The infrared absorption spectrum (KBr) of this product is shown in FIG. 9.

We claim:

1. A condensed azo compound represented by the general formula [I], [II], or [III]:

[I]

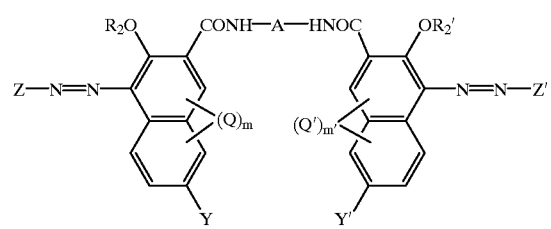

-continued

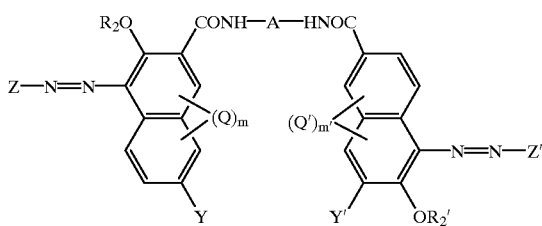
[II]

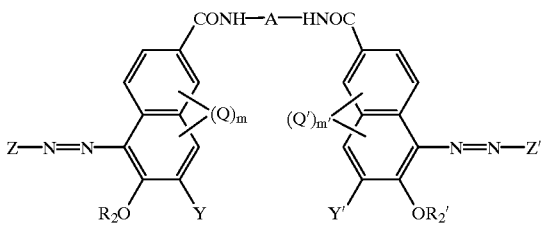
[III]

wherein, Y represents —(CONH)$_n$—X or —COR;

Y' represents —(CONH)$_n$—X' or —COR';

X and X' each represent an optionally branched alkyl group of 1–16 carbon atoms, an optionally substituted aromatic group, or an optionally substituted heterocyclic group having conjugated double bonds;

n represents an integer 1 or 2;

R and R' each represent a hydroxyl group, an optionally branched alkoxy group of 1–30 carbon atoms, a benzyloxy group, a phenyloxy group, or a phenacyloxy group, provided that if one of R and R' is a hydroxyl group, then it may form an acceptable salt;

$R_2$ and $R_2'$ each represent a hydrogen atom, an optionally branched alkyl group of 1–6 carbon atoms, an acyl group of 1–6 carbon atoms, or a phenylalkyl group;

Q and Q' each represent an optionally branched alkyl group of 1–6 carbon atoms, an optionally branched alkoxy group of 1–6 carbon atoms, a halogen atom, a nitro group, or a nitroso group;

m and m' each represent an integer from 0 to 3, provided that if m or m' is 1, then Q or Q' may bind to either of the two fused rings, and if m or m' is 2 or 3, then Q or Q' may bind to one or both of the fused rings or may form a ring together with the two fused rings;

A represents an optionally branched alkylene group of 2–12 carbon atoms or a cyclic group having conjugated double bonds; and Z and Z' each represent an optionally substituted monovalent aromatic group.

2. A condensed azo compound of claim 1 in which A is a group selected from an optionally substituted arylene group, a group represented by the general formula [IV]:

—Ar—M—Ar'— [IV]

[wherein, Ar and Ar' each represent independently an optionally substituted arylene group or a heterocyclic group having conjugated double bonds;

M represents a single bond, or a group selected from —CH$_2$—, —CH=C(E)— (wherein E represents hydrogen, a halogen atom, a lower alkyl group, or a cyano group), —O—, —S—, —S—S—, —CO—, —COO—, —SO$_2$—, —N(T)— (wherein T represents an optionally substituted phenyl group or a lower alkyl group), —N=N—, —CH=CH—φ—CH=CH— (wherein represents an arylene group), and the formula [V]:

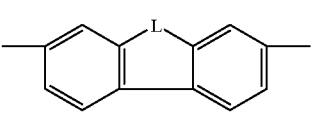
[V]

(wherein, G represents —O—, —S—, or —NH—)], or a group represented by the general formula [VI]:

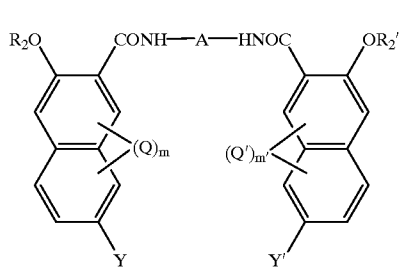
[VI]

[wherein L represents >N—CH$_3$, >C=O, or >C=S.]

3. A condensed azo compound of claim 1 in which Y is —(CONH)$_n$—X and Y' is —(CONH)$_n$—X', wherein n, X, and X' are as defined above.

4. A condensed azo compound of claim 1 in which Z and Z' is an optionally substituted monovalent phenyl group.

5. A pigment which comprises the condensed azo compound of claim 1.

6. A printing ink which comprises the condensed azo compound of claim 1.

7. A coating composition which comprises the condensed azo compound of claim 1.

8. A colorating agent for plastics which comprises the condensed azo compound of claim 1.

9. An organic photoconductive material which comprises the condensed azo compound of claim 1.

10. A process for preparing a condensed azo compound of claim 1, characterized in that an aromatic diazonium compound represented by the general formula [VII] or [VII']:

Z—N$^+$≡N    [VII]

Z'—N$^+$≡N    [VII']

wherein Z and Z' each represent an optionally substituted monovalent aromatic group;

is coupled with a bisamide compound represented by the general formula [VIII], [IX], or [X]:

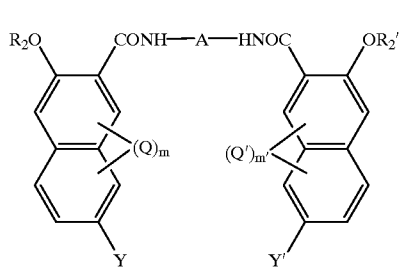
[VIII]

-continued

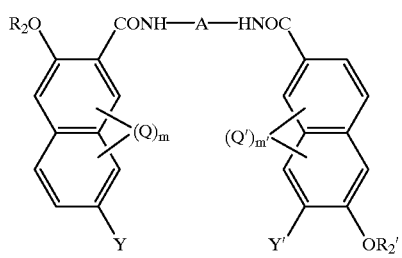
[IX]

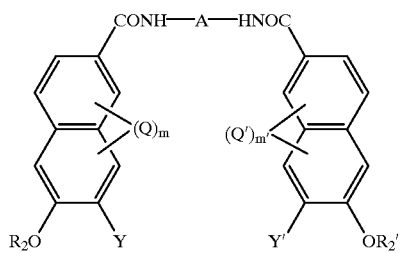
[X]

wherein, Y represents —(CONH)$_n$—X or —COR;

Y' represents —(CONH)$_n$—X' or —COR';

X and X' each represent an optionally branched alkyl group of 1–16 carbon atoms, an optionally substituted aromatic group, or an optionally substituted heterocyclic group having conjugated double bonds;

n represents an integer 1 or 2;

R and R' each represent a hydroxyl group, an optionally branched alkoxy group of 1–30 carbon atoms, a benzyloxy group, a phenyloxy group, or a phenacyloxy group, provided that if one of R and R' is a hydroxyl group, then it may form an acceptable salt;

$R_2$ and $R_2'$ each represent a hydrogen atom, an optionally branched alkyl group of 1–6 carbon atoms, an acyl group of 1–6 carbon atoms, or a phenylalkyl group;

Q and Q' each represent an optionally branched alkyl group of 1–6 carbon atoms, an optionally branched alkoxy group of 1–6 carbon atoms, a halogen atom, a nitro group, or a nitroso group;

m and m' each represent an integer from 0 to 3, provided that if m or m' is 1, then Q or Q' may bind to either of the two fused rings, and if m or m' is 2 or 3, then Q or Q' may bind to one or both of the fused rings or may form a ring together with the two fused rings; and A represents an optionally branched alkylene group of 2–12 carbon atoms or a cyclic group having conjugated double bonds.

11. A bis(aminocarbonylnaphthol) derivative represented by the general formula [VIII'], [IX'], or [X']:

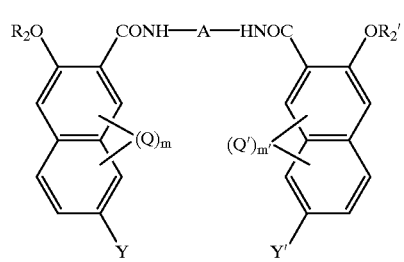
[VIII']

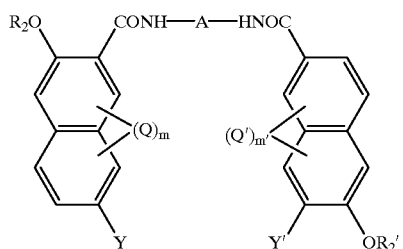
[IX']

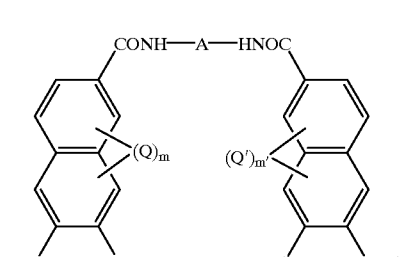
[X']

wherein, Y represents —(CONH)$_n$—X or —COR;

Y' represents —(CONH)$_n$—X' or —COR';

X and X' each represent an optionally branched alkyl group of 1–16 carbon atoms, an optionally substituted aromatic group, or an optionally substituted heterocyclic group having conjugated double bonds;

n represents an integer 1 or 2;

R and R' each represent a hydroxyl group, an optionally branched alkoxy group of 1–6 carbon atoms, a benzyloxy group, a phenyloxy group, or a phenacyloxy group, provided that if one of R and R' is a hydroxyl group, then it may form an acceptable salt;

$R_2$ and $R_2'$ each represent a hydrogen atom, an optionally branched alkyl group of 1–6 carbon atoms, an acyl group of 1–6 carbon atoms, or a phenylalkyl group;

Q and Q' each represent an optionally branched alkyl group of 1–6 carbon atoms, an optionally branched alkoxy group of 1–6 carbon atoms, a halogen atom, a nitro group, or a nitroso group;

m and m' each represent an integer from 0 to 3, provided that if m or m' is 1, then Q or Q' may bind to either of the two fused rings, and if m or m' is 2 or 3, then Q or Q' may bind to one or both of the fused rings or may form a ring together with the two fused rings; and A represents an optionally branched alkylene group of 2–12 carbon atoms or a cyclic group having conjugated double bonds;

provided that, at least one of Y and Y' comprises X or X' which is an optionally branched alkyl group of 1–16 carbon atoms.

12. A bis(aminocarbonylnaphthol) derivative represented by the general formula [VIII"], [XI"], or [X"]:

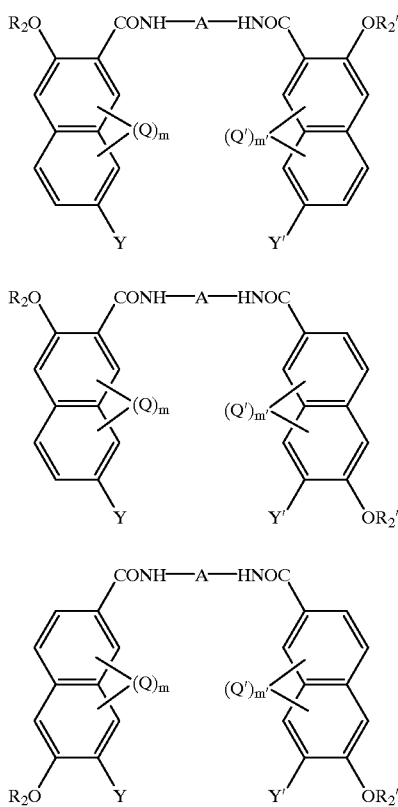

[VIII″]

[IX″]

[X″]

wherein, Y represents —(CONH)$_n$—X or —COR;

Y' represents —(CONH)$_n$—X' or —COR';

X and X' each represent an optionally branched alkyl group of 1–16 carbon atoms, an optionally substituted aromatic group, or an optionally substituted heterocyclic group having conjugated double bonds;

n represents an integer 1 or 2;

R and R' each represent a hydroxyl group, an optionally branched alkoxy group of 7–30 carbon atoms, a benzyloxy group, a phenyloxy group, or a phenacyloxy group, provided that if one of R and R' is a hydroxyl group, then it may form an acceptable salt;

$R_2$ and $R_2$' each represent a hydrogen atom, an optionally branched alkyl group of 1–6 carbon atoms, an acyl group of 1–6 carbon atoms, or a phenylalkyl group;

Q and Q' each represent an optionally branched alkyl group of 1–6 carbon atoms, an optionally branched alkoxy group of 1–6 carbon atoms, a halogen atom, a nitro group, or a nitroso group;

m and m' each represent an integer from 0 to 3, provided that if m or m' is 1, then Q or Q' may bind to either of the two fused rings, and if m or m' is 2 or 3, then Q or Q' may bind to one or both of the fused rings or may form a ring together with the two fused rings; and A represents an optionally branched alkylene group of 2–12 carbon atoms or a cyclic group having conjugated double bonds;

provided that, at least one of Y and Y' comprises R or R' which is an optionally branched alkoxy group of 7–30 carbon atoms.

\* \* \* \* \*